(12) United States Patent
Caplan

(10) Patent No.: US 9,597,385 B2
(45) Date of Patent: Mar. 21, 2017

(54) NANOPARTICLES FOR TREATMENT OF ALLERGY

(71) Applicant: ALLERTEIN THERAPEUTICS, LLC, Fairfield, CT (US)

(72) Inventor: Michael J. Caplan, Woodbridge, CT (US)

(73) Assignee: Allertein Therapeutics, LLC, Fairfield, CT (US)

( * ) Notice: Subject to any disclaimer, the term of this patent is extended or adjusted under 35 U.S.C. 154(b) by 0 days.

(21) Appl. No.: 14/390,365

(22) PCT Filed: Apr. 23, 2013

(86) PCT No.: PCT/US2013/037789
§ 371 (c)(1),
(2) Date: Oct. 2, 2014

(87) PCT Pub. No.: WO2013/163176
PCT Pub. Date: Oct. 31, 2013

(65) Prior Publication Data
US 2015/0174225 A1 Jun. 25, 2015

Related U.S. Application Data

(60) Provisional application No. 61/636,921, filed on Apr. 23, 2012.

(51) Int. Cl.
| | | |
|---|---|---|
| *A61K 39/39* | (2006.01) | |
| *A61K 39/40* | (2006.01) | |
| *A61K 39/02* | (2006.01) | |
| *A61K 39/00* | (2006.01) | |
| *A61K 9/16* | (2006.01) | |

(52) U.S. Cl.
CPC ............... *A61K 39/02* (2013.01); *A61K 9/16* (2013.01); *A61K 39/001* (2013.01); *A61K 2039/55555* (2013.01); *A61K 2039/55561* (2013.01); *A61K 2039/55572* (2013.01); *A61K 2039/55594* (2013.01); *A61K 2039/57* (2013.01); *A61K 2039/58* (2013.01)

(58) Field of Classification Search
None
See application file for complete search history.

(56) References Cited

U.S. PATENT DOCUMENTS

| | | | |
|---|---|---|---|
| 3,977,794 A | 8/1976 | Liedholz | |
| 4,191,743 A | 3/1980 | Klemm et al. | |
| 4,270,537 A | 6/1981 | Romaine | |
| 4,316,885 A | 2/1982 | Rakhit | |
| 4,384,996 A | 5/1983 | Bollinger et al. | |
| 4,596,556 A | 6/1986 | Morrow et al. | |
| 4,650,803 A | 3/1987 | Stella et al. | |
| D296,006 S | 5/1988 | Asche | |
| 4,790,824 A | 12/1988 | Morrow et al. | |
| 4,798,823 A | 1/1989 | Witzel | |
| 4,886,499 A | 12/1989 | Cirelli et al. | |
| 4,894,366 A | 1/1990 | Okuhara et al. | |
| 4,929,611 A | 5/1990 | Okuhara et al. | |
| 4,940,460 A | 7/1990 | Casey et al. | |
| 4,941,880 A | 7/1990 | Burns | |
| 4,956,352 A | 9/1990 | Okuhara et al. | |
| 5,008,110 A | 4/1991 | Benecke et al. | |
| 5,015,235 A | 5/1991 | Crossman | |
| 5,064,413 A | 11/1991 | McKinnon et al. | |
| 5,100,883 A | 3/1992 | Schiehser | |
| 5,118,678 A | 6/1992 | Kao et al. | |
| 5,120,725 A | 6/1992 | Kao et al. | |
| 5,120,727 A | 6/1992 | Kao et al. | |
| 5,120,842 A | 6/1992 | Failli et al. | |
| 5,122,511 A | 6/1992 | Patchett et al. | |
| 5,141,496 A | 8/1992 | Dalto et al. | |
| 5,143,918 A | 9/1992 | Bochis et al. | |
| 5,151,413 A | 9/1992 | Caufield et al. | |
| 5,162,334 A | 11/1992 | Goulet et al. | |
| 5,169,851 A | 12/1992 | Hughes et al. | |

(Continued)

FOREIGN PATENT DOCUMENTS

| | | |
|---|---|---|
| EP | 1752151 A1 | 2/2007 |
| WO | WO-92/05179 A1 | 4/1992 |

(Continued)

OTHER PUBLICATIONS

De Souza Reboucas et al (J. Biomed and Biotech. Jan. 1, 2012, pp. 1-13).*
Bonifaz, L. et al., Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance, The Journal of Experimental Medicine, 196(12):1627-1638 (2002).
Bonifaz, L. et al., In Vivo Targeting of Antigens to Maturing Dendritic Cells via the DEC-205 Receptor Improves T Cell Vaccination, The Journal of Experimental Medicine, 199(6):815-824 (2004).
Gao, X. et al., In vivo cancer targeting and imagin with semiconductor quantum dots, Nature Biotechnology, 22(8):969-976 (2004).
Hawiger, D. et al., Dendritic Cells Induce Peripheral T Cell Unresponsiveness Under Steady State Conditions In Vivo, The Journal of Experimental Medicine, 194(6):769-779 (2001).

(Continued)

*Primary Examiner* — Jennifer Graser
(74) *Attorney, Agent, or Firm* — Choate, Hall & Stewart LLP; Brenda Herschbach Jarrell; Brian E. Reese

(57) ABSTRACT

The present invention encompasses the surprising finding that nanoparticle compositions can have beneficial effects on allergy even when prepared without a known specific allergy therapeutic. The present invention provides such nanoparticle compositions. In some embodiments, provided nanoparticles are associated with functional elements that cause the nanoparticles to mimic bacterial cells. The present invention encompasses the surprising finding that provided nanoparticles may be useful for treatment and/or prevention of multiple different allergies in a single patient. The present invention encompasses the recognition that provided empty nanoparticles may be useful as a "pan-allergy" therapeutic and/or vaccine.

7 Claims, No Drawings

(56) References Cited

U.S. PATENT DOCUMENTS

| | | |
|---|---|---|
| 5,189,042 A | 2/1993 | Goulet et al. |
| 5,190,521 A | 3/1993 | Hubbard et al. |
| 5,202,332 A | 4/1993 | Hughes et al. |
| 5,208,228 A | 5/1993 | Ok et al. |
| 5,208,241 A | 5/1993 | Ok et al. |
| 5,225,194 A | 7/1993 | Suer |
| 5,227,467 A | 7/1993 | Durette et al. |
| 5,250,678 A | 10/1993 | Goulet et al. |
| 5,254,562 A | 10/1993 | Okuhara et al. |
| 5,258,389 A | 11/1993 | Goulet et al. |
| 5,262,533 A | 11/1993 | Sinclair et al. |
| 5,284,826 A | 2/1994 | Eberle |
| 5,284,840 A | 2/1994 | Rupprecht et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,504,091 A | 4/1996 | Molnar-Kimber et al. |
| 5,520,639 A | 5/1996 | Peterson et al. |
| 5,527,288 A | 6/1996 | Gross et al. |
| 5,532,248 A | 7/1996 | Goulet et al. |
| 5,543,158 A | 8/1996 | Gref et al. |
| 5,558,869 A | 9/1996 | Burks, Jr. et al. |
| 5,569,189 A | 10/1996 | Parsons |
| 5,591,767 A | 1/1997 | Mohr et al. |
| 5,599,302 A | 2/1997 | Lilley et al. |
| 5,649,912 A | 7/1997 | Peterson |
| 5,683,712 A | 11/1997 | Cavazza |
| 5,693,648 A | 12/1997 | Goulet et al. |
| 5,704,911 A | 1/1998 | Parsons |
| 5,709,797 A | 1/1998 | Bocchiola et al. |
| 5,739,432 A | 4/1998 | Sinha |
| 5,753,234 A | 5/1998 | Lee et al. |
| 5,774,209 A | 6/1998 | Shestock |
| 5,830,877 A | 11/1998 | Carson et al. |
| 5,893,397 A | 4/1999 | Peterson et al. |
| 5,948,433 A | 9/1999 | Burton et al. |
| 5,962,566 A | 10/1999 | Grandfils et al. |
| 5,965,154 A | 10/1999 | Haralambopoulos |
| 5,972,366 A | 10/1999 | Haynes et al. |
| 5,973,121 A | 10/1999 | Burks, Jr. et al. |
| 5,993,412 A | 11/1999 | Deily et al. |
| 6,010,715 A | 1/2000 | Wick et al. |
| 6,136,357 A | 10/2000 | Dietl |
| 6,238,925 B1 | 5/2001 | Sampson |
| 6,475,995 B1 | 11/2002 | Roy et al. |
| 6,486,311 B1 | 11/2002 | Burks, Jr. et al. |
| 6,503,921 B2 | 1/2003 | Naicker et al. |
| 6,544,543 B1 | 4/2003 | Mandrusov et al. |
| 6,551,990 B2 | 4/2003 | Giachelli et al. |
| 6,628,382 B2 | 9/2003 | Robertson |
| 6,676,963 B1 | 1/2004 | Lanza et al. |
| 6,793,938 B2 | 9/2004 | Sankaram |
| 6,809,826 B2 | 10/2004 | Robertson |
| 6,835,824 B1 | 12/2004 | Burks, Jr. et al. |
| 7,081,489 B2 | 7/2006 | Chen et al. |
| 7,397,036 B2 | 7/2008 | Robertson et al. |
| 7,485,708 B2 | 2/2009 | Burks, Jr. et al. |
| 7,534,448 B2 | 5/2009 | Saltzman et al. |
| 7,534,449 B2 | 5/2009 | Saltzman et al. |
| 7,550,154 B2 | 6/2009 | Saltzman et al. |
| 8,802,375 B2 | 8/2014 | Sampson et al. |
| 8,815,251 B2 | 8/2014 | Caplan et al. |
| 8,889,117 B2 | 11/2014 | Mellman et al. |
| 2001/0051155 A1 | 12/2001 | Sosin et al. |
| 2002/0009452 A1 | 1/2002 | Caplan |
| 2002/0044959 A1 | 4/2002 | Goetz et al. |
| 2002/0076420 A1 | 6/2002 | Caplan et al. |
| 2002/0132763 A1 | 9/2002 | Naicker et al. |
| 2002/0155607 A1 | 10/2002 | Boutin |
| 2003/0003591 A1 | 1/2003 | LaCourt et al. |
| 2003/0035810 A1 | 2/2003 | Caplan |
| 2003/0202980 A1 | 10/2003 | Caplan et al. |
| 2003/0235619 A1 | 12/2003 | Allen et al. |
| 2004/0022840 A1 | 2/2004 | Nagy et al. |
| 2004/0023897 A1 | 2/2004 | Caplan |
| 2004/0156821 A1 | 8/2004 | Bottomly et al. |
| 2004/0208894 A1 | 10/2004 | Caplan |
| 2004/0234548 A1 | 11/2004 | Caplan |
| 2006/0002852 A1 | 1/2006 | Saltzman et al. |
| 2006/0002971 A1 | 1/2006 | Saltzman et al. |
| 2006/0051426 A1 | 3/2006 | Golomb et al. |
| 2006/0077390 A1 | 4/2006 | Kralik |
| 2006/0087650 A1 | 4/2006 | Shen |
| 2006/0109468 A1 | 5/2006 | Evans |
| 2006/0246139 A1 | 11/2006 | Miyaji et al. |
| 2007/0092575 A1 | 4/2007 | Balaban et al. |
| 2007/0148074 A1 | 6/2007 | Sadoqi et al. |
| 2007/0184068 A1 | 8/2007 | Renner et al. |
| 2007/0213507 A1 | 9/2007 | Burks et al. |
| 2007/0224225 A1 | 9/2007 | Irache Garreta et al. |
| 2008/0014144 A1 | 1/2008 | Saltzman et al. |
| 2008/0249014 A1 | 10/2008 | Tauer et al. |
| 2009/0011993 A1 | 1/2009 | Murthy et al. |
| 2009/0239789 A1 | 9/2009 | Saltzman et al. |
| 2009/0269397 A1 | 10/2009 | Saltzman et al. |
| 2010/0031262 A1 | 2/2010 | Baird-Gent |
| 2010/0104503 A1 | 4/2010 | Mellman et al. |
| 2010/0151436 A1 | 6/2010 | Fong et al. |
| 2010/0166802 A1 | 7/2010 | Caplan et al. |
| 2010/0233251 A1 | 9/2010 | Von Andrian et al. |
| 2010/0233521 A1 | 9/2010 | Byun et al. |
| 2010/0284965 A1 | 11/2010 | Fahmy et al. |
| 2011/0027298 A1 | 2/2011 | Caplan et al. |
| 2011/0218396 A1 | 9/2011 | Williams et al. |
| 2011/0293705 A1 | 12/2011 | Irvine et al. |
| 2012/0276156 A1 | 11/2012 | Fraser et al. |
| 2013/0302409 A1 | 11/2013 | Fuchs et al. |
| 2015/0118318 A1 | 4/2015 | Fahmy et al. |
| 2015/0125384 A1 | 5/2015 | Mellman et al. |
| 2015/0153358 A1 | 6/2015 | Ayuso et al. |
| 2015/0231266 A1 | 8/2015 | Metcalfe et al. |
| 2015/0366994 A1 | 12/2015 | Metcalfe et al. |
| 2016/0054315 A1 | 2/2016 | Fahmy et al. |
| 2016/0113881 A1 | 4/2016 | Sosin et al. |
| 2016/0213761 A1 | 7/2016 | Fahmy et al. |
| 2016/0228521 A1 | 8/2016 | Sosin et al. |

FOREIGN PATENT DOCUMENTS

| | | |
|---|---|---|
| WO | WO-95/03356 A1 | 2/1995 |
| WO | WO-95/03357 A1 | 2/1995 |
| WO | WO-96/02555 A1 | 2/1996 |
| WO | WO-96/20698 A2 | 7/1996 |
| WO | WO-97/13537 A1 | 4/1997 |
| WO | WO-97/37705 A1 | 10/1997 |
| WO | WO-98/16247 A1 | 4/1998 |
| WO | WO-98/18810 A1 | 5/1998 |
| WO | WO-98/40100 A1 | 9/1998 |
| WO | WO-99/34850 A1 | 7/1999 |
| WO | WO-99/52550 | 10/1999 |
| WO | WO-00/29043 A1 | 5/2000 |
| WO | WO-00/37067 A2 | 6/2000 |
| WO | WO-00/54803 A2 | 9/2000 |
| WO | WO-01/39800 A2 | 6/2001 |
| WO | WO-02/067849 A2 | 9/2002 |
| WO | WO-02/076441 A1 | 10/2002 |
| WO | WO-03/087021 A2 | 10/2003 |
| WO | WO-2004/071493 A1 | 8/2004 |
| WO | WO-2005/021730 A2 | 3/2005 |
| WO | WO-2006/037979 A2 | 4/2006 |
| WO | WO-2006/050170 A2 | 5/2006 |
| WO | WO-2006/052285 A2 | 5/2006 |
| WO | WO-2006/080951 A8 | 8/2006 |
| WO | WO-2008/109347 A2 | 9/2008 |
| WO | WO-2008/115641 A2 | 9/2008 |
| WO | WO-2008/121949 A1 | 10/2008 |
| WO | WO-2009/038591 A1 | 3/2009 |
| WO | WO-2009/094273 A2 | 7/2009 |

(56) References Cited

FOREIGN PATENT DOCUMENTS

| | | |
|---|---|---|
| WO | WO-2010/003009 A2 | 1/2010 |
| WO | WO-2010/042870 A1 | 4/2010 |
| WO | WO-2011/150235 A1 | 12/2011 |
| WO | WO-2012/167261 A2 | 12/2012 |
| WO | WO-2013/003157 A1 | 1/2013 |
| WO | WO-2015/066535 A1 | 5/2015 |
| WO | WO-2015/175597 A1 | 11/2015 |

OTHER PUBLICATIONS

Hawker, C.J. and Wooley, K.L., The Convergence of Synthetic Organic and Polymer Chemistries, Science, 309:1200-1205 (2005).
Heffernan, M.J. and Murthy, N., Polyketal Nanoparticles: A New pH-Sensitive Biodegradable Drug Delivery Vehicle, Bioconjugate Chemistry, 16:1340-1342 (2005).
Jain, R.A., The manufacturing techniques of various drug loaded biodegradable poly(lactide-co-glycolide) (PLGA) devices, Biomaterials, 21:2475-2490 (2000).
Li, Z. et al., Surface Functionalization of Ordered Mesoporous Carbons—A Comparative Study, Langmuir, 21:11999-12006 (2005).
Mathiowitz, E. and Langer, R., Polyanhydride Microspheres as Drug Carriers I. Hot-Melt Microencapsulation, Journal of Controlled Release, 5:13-22 (1987).
Mathiowitz, E. et al., Novel Microcapsules for Delivery Systems, Reactive Polymers, 6:275-283 (1987).
Mathiowitz, E. et al., Polyanhydride Microspheres as Drug Carriers II. Microencapsulation by Solvent Removal, Journal of Applied Polymer Science, 35:755-774 (1988).
Moser, C. et al., Virosomal adjuvanted antigen delivery systems, Expert Reviews in Vaccines, 2(2):189-196 (2003).
Murray, C.B. et al., Synthesis and Characterization of Monodisperse Nanocrystals and Close-Packed Nanocrystal Assemblies, Annual Reviews of Material Science, 30:545-610 (2000).
O'Hagan and Valiante, 2003, Nat. Rev. Drug Discov., 2:727-35.
O'Reilly, R.K. et al., Functionalization of Micelles and Shell Cross-linked Nanoparticles Using Click Chemistry, Chemistry Materials, 17:5976-5988 (2005).
Pellegrino, T. et al., On the Development of Colloidal Nanoparticles towards Multifunctional Structures and their Possible Use for Biological Applications, Small, 1(1):48-63 (2005).
Sussman, G.L. et al., The Spectrum of IgE-Mediated Responses to Latex, The Journal of the American Medical Association, 265(21):2844-2847 (1991).
Trindade, T. et al., Nanocrystalline Semiconductors: Synthesis, Properties, and Perspectives, Chemistry Materials, 13:3843-3858 (2001).
Van Der Lubben, I.M. et al., Chitosan for mucosal vaccination, Advanced Drug Delivery Reviews, 52:139-144 (2001).
Wagener and Gomez, ADMET Polymerization, in Encyclopedia of Materials: Science and Technology, E. J. Kramer and C. Hawker, Editors, Elsevier, Oxford, 5, 48 (2002).
Wikingsson, L.D. and Sjöholm, I., Polyacryl starch microparticles as adjuvant in oral immunisation inducing mucosal and systemic immune responses in mice, Vaccine, 20:3355-3363 (2002).
Anderson and Shive, et al., Biodegradation and biocompatibility of PLA and PLGA microspheres, Adv Drug Deliv Rev, 28(1):5-24 (1997).
Apostolopoulos, V. et al., Structural implications for the design of molecular vaccines, Curr. Opin. Mol. Ther., 2(1): 29-36 (2000).
Aziz et al., Oral Vaccines: New Needs, New Possibilities, BioEssays, 29(6): 591-604 (2007).
Blanchette et al., Cellular evaluation of oral chemotherapy carriers, J. Biomed. Mater. Res. A, 72(4): 381-388 (2005).
Blanchette et al., Oral chemotherapeutic delivery: design and cellular response, Ann. Biomed. Eng., 33(2): 142-149 (2005).
Bourges et al., Ocular drug delivery targeting the retina and retinal pigment epithelium using polylactide nanoparticles, Invest Ophthalmol Vis Sci, 44:3562-3569 (2003).
Bourla et al., Age-related macular degeneration: a practical approach to a challenging disease, J. Am. Geriatr. Soc., 54: 1130-1135 (2006).
Bramwell et al., The rational design of vaccines, Drug Discovery Today, 10(22): 1527-1534 (2005).
Brigger et al., Nanoparticles in cancer therapy and diagnosis, Adv Drug Deliv Rev, 54:631-651 (2002).
Brunner et al., pH and osmotic pressure inside biodegradable microspheres during erosion, Pharm Res, 16(6):847-53 (1999).
Calvo et al., Chitosan and chitosan/ethylene oxide-propylene oxide block copolymer nanoparticles as novel carriers for proteins and vaccines. Pharm. Res., 14(10): 1431-1436 (1997).
Cannizzaro, et al., A novel biotinylated degradable polymer for cell-interactive applications, Biotech Bioeng., 58(5): 529-535 (1998).
Cao et al., Production and surface modification of polylactide-based polymeric scaffolds for soft-tissue engineering, Methods Mol. Biol., 238:87-112 (2004).
Caponetti et al., Microparticles of novel branched copolymers of lactic acid and amino acids: preparation and characterization, J Pharm Sci, 88(1):136-41 (1999).
Challacombe et al., Enhanced secretory IgA and systemic IgG antibody responses after oral immunization with biodegradable microparticles containing antigen, Immunology, 76(1): 164-168 (1992).
Cho et al., Receptor-mediated delivery of all trans-retinoic acid to hepatocyte using poly(L-lactic acid) nanoparticles coated with galactose-carrying polystyrene, J Control Release, 77:7-15 (2001).
Cremaschi et al., Different kinds of polypeptides and polypeptide-coated nanoparticles are accepted by the selective transcytosis shown in the rabbit nasal mucosa, Biochim. Biophys. Acta, 1416(1-2): 31-38 (1999).
Cremaschi et al., Further analysis of transcytosis of free polypeptides and polypeptide-coated nanobeads in rabbit nasal mucosa, J. Appl. Physiol., 91(1): 211-217 (2001).
Croll, Controllable surface modification of poly(lactic-co-glycolic acid) (PLGA) by hydrolysis or aminolysis 1: physical, chemical, and theoretical aspects, Biomacromolecules, 5(2):463-73 (2004).
Cui et al., Intradermal immunization with novel plasmid DNA-coated nanoparticles via a needle-free injection device, J. Biotechnology, 102(2): 105-115 (2003).
De Kozak, Intraocular injection of tamoxifen-loaded nanoparticles: a new treatment of experimental autoimmune uveoretinitis, Eur J Immunol, 34:3702-3712 (2004).
Demento et al., Inflammasome-activating nanoparticles as modular systems for optimizing vaccine efficacy, Vaccine, 27(23): 3013-3021 (2009).
Demento et al., TLR9-Targeted Biodegradable Nanoparticles as Immunization Vectors Protect Against West Nile Encephalitis, J. Immunol., 185: 2989-2997 (2010).
Dev et al., Kinetics of drug delivery to the arterial wall via polyurethane-coated removable nitinol stent: comparative study of two drugs, Catheterization and Cardiovascular Diagnosis, 34(3): 272-8 (1995).
Dev et al., Sustained local drug delivery to the arterial wall via biodegradable microspheres, Catheterization and Cardiovascular Diagnosis, 41(3): 324-32 (1997).
Edelman et al., Effect of controlled adventitial heparin delivery on smooth muscle cell proliferation following endothelial injury, Proc Nat. Aca. Sci, U.S.A., 87(10): 3773-7 (1990).
Edwards et al., Complement Factor H Polymorphism and Age-Related Macular Degeneration, Science, 308(5720):421-4 (2005).
Elamanchili et al., Characterization of poly(D,L-lactic-co-glycolic acid) based nanoparticulate system for enhanced delivery of antigens to dendritic cells, Vaccine, 22: 2406•2412 (2004).
Eldridge et al., Biodegradable and biocompatible poly(DL-lactide-co-glycolide) microspheres as an adjuvant for staphylococcal enterotoxin B toxoid which enhances the level of toxin-neutralizing antibodies, Infection and Immunity, 59(9): 2978-2986 (1991).
Eldridge et al., Biodegradable microspheres—Vaccine delivery system for oral immunization, Current Topics in Microbiology and Immunology, 146: 59-66 (1989).

(56) References Cited

OTHER PUBLICATIONS

Eldridge et al., Controlled vaccine release in the gut-associated lymphoid tissues. I. Orally-administered biodegradable microspheres target the Peyer's patches, J. Control. Release, 11(1-3): 205-214 (1990).
Eliaz and Szoka, Liposome-encapsulated doxorubicin targeted to CD44: a strategy to kill CD44-overexpressing tumor cells, Cancer Res, 61: 2592-2601 (2001).
Eniola et al., Artificial polymeric cells for targeted drug delivery, J Control Release, 87(1-3): 15-22 (2003).
Escribano, M.M. et al., Anaphylactic reaction cause by cherry ingestion, Allergy 51(10): 756-757 (1996).
Evora et al., Relating the phagocytosis of microparticles by alveolar macrophages to surface chemistry: the effect of 1,2-dipalmitoylphosphatidylcholine, J Control Release, 51 (2-3):143-52 (1998).
Fahmy et al., Surface modification of biodegradable polyesters with fatty acid conjugates for improved drug targeting, Biomaterials, 26(28): 5727-5736 (2005).
Fahmy et al., Targeted for drug delivery, Materials Today, 8(8, Supplement 1): 18-26 (2005).
Fahmy, et al., Increased TCR avidity after T cell activation: a mechanism for sensing low-density antigen, Immunity, 14:135-43 (2001).
Faraasen et al., Ligand-specific targeting of microspheres to phagocytes by surface modification with poly(L-lysine)-grafted poly(ethylene glycol) conjugate, Pharm Res, 20(2): 237-46 (2003).
Fischer, N. O. et al., Conjugation to nickel-chelating nanolipoprotein particles increases the potency and efficacy of subunit vaccines to prevent West Nile encephalitis, Bioconjugate Chemistry, 21(6): 1018-1022 (2010).
Friede et al., Need for new vaccine formulations and potential of particulate antigen and DNA delivery systems, Adv. Drug Deliv. Re., 57(3): 325-331 (2005).
Garcia-Garcia et al., Drug-eluting stents, Arch. Cardiol. Mex., 76(3): 297-319 (2006).
Gomez, S. et al., Allergen Immunotherapy With Nanoparticles Containing Lipopolysaccharide A From Brucella Ovis, European Journal of Pharmaceutics and Biopharmaceutics, 70: 711-717 (2008).
Gomez, S. et al., Gantrez AN Nanoparticles as an Adjuvant for Oral Immunotherapy with Allergens, Vaccine, 25: 5263-5271 (2007).
Gref, R., 'Stealth' corona-core nanoparticles surface modified by polyethylene glycol (PEG): influences of the corona (PEG chain length and surface density) and of the core composition on phagocytic uptake and plasma protein adsorption, Colloids and Surfaces B: Biointerfaces, 18(3-4): 301-313 (2000).
Gref, R., Surface-engineered nanoparticles for multiple ligand coupling, Biomaterials, 24(24): 4529-4537 (2003).
Gupta et al., Adjuvants for human vaccines current status, problems, and future prospects, Vaccine, 13(14): 1263-1276 (1995).
Gupta et al., Poly(lactide-co-glycolide) microparticles for the development of single-dose controlled-release vaccines, Adv. Drug Deliv. Rev., 32(3): 225-246 (1998).
Guzman et al., Local intraluminal infusion of biodegradable polymeric nanoparticles, Circulation 94: 1441-1448 (1996).
Haines et al., Complement factor H variant increases the risk of age-related macular degeneration, Science, 308(5720):419-21 (2005).
Hallahan et al., Integrin-mediated targeting of drug delivery to irradiated tumor blood vessels, Cancer Cell, 3:6374 (2003).
Hammer et al., Synthetic cells-self-assembling polymer membranes and bioadhesive colloids, Annu. Rev. Mater. Res., 31:387-40 (2001).
Hariharan et al., Improved graft survival after renal transplantation in the United States, 1988 to 1996, N. Eng. J. Med., 342(9):605-12 (2000).
Hattori et al., Enhanced in vitro DNA transfection efficiency by novel folate-linked nanoparticles in human prostate cancer and oral cancer, Journal of Controlled Release, 97: 173-183 (2004).
Hood et al., Tumor regression by targeted gene delivery to the neovasculature, Science, 296(5577):2404-2407 (2002).
Huang, Monoclonal antibody covalently coupled with fatty acid. A reagent for in vitro liposome targeting, J. Biol. Chem., 255(17):8015-8 (1980).
Humphrey, The effect of intramural delivery of polymeric nanoparticles loaded with the antiproliferative 2-aminochromone U-86983 on neointimal hyperplasia development in balloon-injured porcine coronary arteries, Adv. Drug Del. Rev., 24: 87-108 (1997).
International Search Report for PCT/US2005/023444, 3 pages (Sep. 26, 2007).
International Search Report for PCT/US2008/054086, 3 pages (Sep. 22, 2008).
International Search Report for PCT/US2013/037789, 3 pages (Aug. 30, 2013).
International Search Report for PCT/US2014/055625, 3 pages (Dec. 8, 2014).
International Search Report for PCT/US2014/032838, 4 pages (Sep. 4, 2014).
International Search Report for PCT/US2015/059711, 8 pages (May 12, 2016).
Italia et al., Disease, destination, dose and delivery aspects of ciclosporin: the state of the art, Drug Discov. Today, 11(17-18): 846-854 (2006).
Jansen et al., Encapsulation of Guest Molecules into a Dendritic Box, Science, 266(5188): 1226-1229 (1994).
Jansen et al., The Dendritic Box: Shape-Selective Liberation of Encapsulated Guests, Journal of the American Chemical Society, 117:4417-4418 (1995).
Johansen et al., Revisiting PLA/PLGA microspheres: an analysis of their potential in parenteral vaccination, Eur J Pharm Biopharm, 50(1):129-46 (2000).
Keegan et al., Biodegradable Microspheres with Enhanced Capacity for Covalently Bound Surface Ligands Macromolecules, 37:9979-84 (2004).
Keegan et al., Biomimetic design in microparticulate vaccines, Biomaterials, 24(24):4435-4443 (2003).
Klein et al., Complement factor H polymorphism in age-related macular degeneration, Science, 308(5720):385-9 (2005).
Klimek, L. et al., Assessment of clinical efficacy of CYT003-QbG10 in patients with allergic rhinoconjunctivitis: a phase IIb study, Clinical & Experimental Allergy, 41(9): 1305-1312 (2011).
Kobayashi et al., Dendrimer-based Macromolecular MRI Contrast Agents: Characteristics and Application, Mol Imaging, 2:1-10 (2003).
Kobayashi, Evaluation of the in vivo biodistribution of indium-111 and yttrium-88 labeled dendrimer-1 B4M-DTPA and its conjugation with anti-Tac monoclonal antibody, Bioconjug Chem, 10: 103-11 (1999).
Kohn et al., Single-step immunization using a controlled release, biodegradable polymer with sustained adjuvant activity, J. Immunol. Methods, 95(1): 31-38 (1986).
Kompella et al., Subconjuctival nano- and microparticles sustain retinal delivery of budesonide, a corticosteroid capable of inhibiting VEGF expression, Invest Ophthalmol. Vis. Sci., 44: 1192-1201 (2003).
Kono et al., Abstracts of Papers of the American Chemical Society, 221: U377-U377 (2001).
Kwon et al., Enhanced antigen presentation and immunostimulation of dendritic cells using acid degradable cationic nanoparticles, J. Control Release, 105(3): 119-212 (2005).
Labhasetwar et al., Arterial uptake of biodegradable nanoparticles: effect of surface modifications, J Pharm Sci, 87:1229-1234 (1998).
Labhasetwar, et al., Nanoparticle drug delivery system for restenosis, Advanced Drug Delivery Reviews, 24:63-85 (1997).
Lamprecht et al., Biodegradable nanoparticles for targeted drug delivery in treatment of inflammatory bowel disease, J Pharmacol Exp Ther, 299(2):775-81 (2001).
Langer and Folkman, Polymers for the sustained release of proteins and other macromolecules, Nature, 263(5580): 797-800 (1976).
Hanes, J. et al., New advances in microsphere-based single-dose vaccines, Adv. Drug Deliv. Rev., 28(1): 97-119 (1997).

(56) References Cited

OTHER PUBLICATIONS

Lathia et al., Polymeric contrast agent with targeting potential., Ultrasonics, 42(1-9):763-8 (2004).
Lavik et al., A simple synthetic route to the formation of a block copolymer of poly(lactic-coglycolic acid) and polylysine for the fabrication of functionalized, degradable structures for biomedical applications, J Biomed Mater Res, 58(3):291-4 (2001).
Linblad, E.B., Aluminum adjuvants—in retrospect and prospect, Vaccine, 22(27-28): 3658-3668 (2004).
Liu, Y. et al., Stability and Ostwald ripening of block copolymer stabilized nanoparticles, Abstracts of Papers of the American Chemical Society, The 230th ACS National Meeting, Washington, DC, COLL 402, 1 page (Sep. 1, 2005). URL: http://oasys2.confex.com/acs/230nm/techprogram/P862384.HTM. [Retrieved Apr. 29, 2016].
Lopes De Menezes et al., In vitro and in vivo targeting of immunoliposomal doxorubicin to human B-cell lymphoma, Cancer Res, 58:3320-3330 (1998).
Luo, D. et al., Controlled DNA delivery systems, Phar. Res., 16: 1300-1308 (1999).
Luo, D. et al., Poly(ethylene glycol)—Conjugated PAMAM Dendrimer for Biocompatible, High-Efficiency DNA Delivery, Macromolecules, 35:3456-3462 (2002).
Mader et al., Monitoring microviscosity and microacidity of the albumin microenvironment inside degrading microparticles from poly(lactide-co-glycolide) (PLG) or ABA-triblock polymers containing hydrophobic poly(lactide-co-glycolide) A blocks and hydrophilic poly(ethyleneoxide) B blocks, Pharm Res, 15(5):787-93 (1998).
Mainardes et al., Colloidal carriers for ophthalmic drug delivery, Curr Drug Targets, 6:363-371 (2005).
Mallajosyula, J.K. et al., Single-dose monomeric HA subunit vaccine generates full protection from influenza challenge, Human Vaccines & Immunotherapeutics, 1(3): 586-595 (2013).
Maloy et al., Induction of mucosal and systemic immune responses by immunization with ovalbumin entrapped in poly(lactide-co-glycolide) microparticles, Immunology, 81(4): 661-667 (1994).
Marx et al., Protection against vaginal SIV transmission with microencapsulated vaccine, Science, 260(5112): 1323-1327 (1992).
McPhail, D. et al., Liposomes encapsulating polymeric chitosan based vesicles—a vesicle in vesicle system for drug delivery, International Journal of Pharmaceutics, 200(1):73-86 (2000).
Mellman, I., Antigen processing and presentation by dendritic cells: cell biological mechanisms, Adv. Exp. Med. Biol., 560: 63-67 (2005).
Mellman, I., and Steinman, R.M., Dendritic cells: specialized and regulated antigen processing machines, Cell, 106(3): 255-258 (2001).
Myers, E.W. and Miller, W., Optimal alignments in linear space, Comput. Appl. Biosci., 4(1): 11-17 (1988).
Mu et al., A novel controlled release formulation for the anticancer drug paclitaxel (Taxol®); PLGA nanoparticles containing vitamin E TPGS, J Control Release, 86(1):33-48 (2003).
Mu et al., Vitamin E TPGS used as emulsifier in the solvent evaporation/extraction technique for fabrication of polymeric nanospheres for controlled release of paclitaxel (Taxol®), J Control Release, 80(1-3): 129-44 (2002).
Mumper et al., Genetic immunization by jet injection of targeted pDNA-coated nanoparticles, Methods, 31(3): 255-262 (2003).
Müller, et al., Surface Modification of PLGA Microspheres, J Biomed Mater Res, 66A(1):55-61 (2003).
Naylor et al., Starburst Dendrimers. 5. Molecular Shape Control, Journal of the American Chemical Society, 111:2339-2341 (1989).
Nellore et al., Evaluation of biodegradable microspheres as vaccine adjuvant or hepatitis B surface antigen, J. Parenter. Sci. Technol., 46(5): 176-180 (1992).
Nunn et al., Complement inhibitor of C5 activation from the soft tick Ornithodoros moubata, J Immunol, 174(4):2084-91 (2005).

O'Hagan et al., Long-term antibody responses in mice following subcutaneous immunization with ovalbumin entrapped in biodegradable microparticles, Vaccine, 11(9): 965-969 (1993).
Olivier, J.C., Drug transport to brain with targeted nanoparticles, NeuroRx, 2:108-119 (2005).
Pan et al., Strategy for the treatment of acute myelogenous leukemia based on folate receptor β-targeted liposomal doxorubicin combined with receptor induction using all-trans retinoic acid, Blood, 100: 594-602 (2002).
Panyam, et al., Biodegradable nanoparticles for drug and gene delivery to cells and tissue, Adv Drug Deliv Rev, 55(3):329-47 (2003).
Park et al., Anti-HER2 immunoliposomes: enhanced efficacy attributable to targeted delivery, Clin Cancer Res, 8:1172-1181(2002).
Park et al., Integration of surface modification and 3D fabrication techniques to prepare patterned poly(L-lactide) substrate allowing regionally selective cell adhesion, J Biomater Sci Polym Ed, 9(2):89-110 (1998).
Park et al., Surface modified poly(lactide-co-glycolide) nanospheres for targeted bone imaging with enhanced labeling and delivery of radio isotope, J Biomed Mater Res, 67 A(3):751-60 (2003).
Pashine et al., Targeting the innate immune response with improved vaccine adjuvants, Nat. Med., 11(4 Suppl): S63-S68 (2005).
Pastorino et al., Doxorubicin-loaded Fab' Fragments of Anti-disialoganglioside immunoliposomes selectively inhibit the growth and dissemination of human neuroblastoma in nude mice, Cancer Research, 63: 86-92 (2003).
Pitaksuteepong et al., Uptake of antigen encapsulated in polyethylcyanoacrylate nanoparticles by D1-dendtitic cells, Pharmazie, 59(2): 134-142 (2004).
Quirk et al., Cell-type-specific adhesion onto polymer surfaces from mixed cell populations, Biotech. Bioeng., 81(5):625-628 (2003).
Schiffelers et al., Cancer siRNA therapy by tumor selective delivery with ligand-targeted sterically stabilized nanoparticle, Nucleic Acids Res, 32: e149 (2004).
Schneck, J.P., Monitoring antigen-specific T cells using MHC-Ig dimers, Immunol. Invest., 29:163-9 (2000).
Schöll, I. et al., Biodegradable PLGA Particles for Improved Systemic and Mucosal Treatment of Type I Allergy, Immunol. Allergy Clin. N. Am., 26(2): 349-364 (2006).
Sesardic et al., European union regulatory developments for new vaccine adjuvants and delivery systems, Vaccine, 22(19): 2452-2456 (2004).
Shastri, N., Needles in haystacks: identifying specific peptide antigens for T cells, Curr. Opin. Immunol., 8(2): 271-277 (1996).
Shen et al., Enhanced and prolonged cross-presentation following endosomal escape of exogenous antigens encapsulated in biodegradable nanoparticles, Immunity, 117(1): 78-88 (2006).
Shenderova et al., The acidic microclimate in poly(lactide-co-glycolide) microspheres stabilizes camptothecins, Pharm Res, 16(2):241-248 (1999).
Silin, D.S. and Lyubomska, V., Overcoming immune tolerance during oral vaccination against actinobacillus pleuropneumoniae, J. Vet. Med. B. Infect. Dis. Vet. Public Health, 49(4): 169-175 (2002).
Silin, D.S. et al., Oral Vaccination: Where are we?, Exp. Opin. Drug Deliv., 4(4): 323-340 (2007).
Singh et al., Advances in vaccine adjuvants for infectious diseases, Curr. HIV Res., 1(3): 309-20 (2003).
Singh et al., Controlled release microparticles as a single dose diphtheria toxoid vaccine: immunogenicity in small animal models, Vaccine, 16(4): 346-352 (1998).
Singh et al., Immunogenicity and protection in small-animal models with controlled-release tetanus toxoid microparticles as a single-dose vaccine, Infect. Immun., 65(5): 1716-1721 (1997).
Singh et al., Immunogenicity studies on diphtheria toxoid loaded biodegradable microspheres, Int. J. Pharmaceutics, 85(1-3): R5-R8 (1992).
Singh, M. and O'Hagan, D.T., Recent advances in vaccine adjuvants, Pharm. Res., 19(6): 715-728 (2002).
Song et al., Arterial uptake of biodegradable nanoparticles for intravascular local drug delivery: results with an acute dog model, J Control Release, 54: 201-211 (1998).

(56) References Cited

OTHER PUBLICATIONS

Storni et al., Immunity in response to particulate antigen delivery systems, Adv. Drug Deliv. Rev., 57(3): 333-55 (2005).
Summerton, J.E., Endo-Porter: A Novel Reagent for Safe, Effective Delivery of Substances into Cells, Ann. N. Y. Acad. Sci., 1058: 1-14 (2005).
Supplementary Partial European Search Report for EP 13781604, 7 pages (Oct. 14, 2015).
Sykulev et al., High-affinity reactions between antigen-specific T-cell receptors and peptides associated with allogeneic and syngeneic major histocompatibility complex class I proteins, Proc Natl Acad Sci US A, 91: 11487-11491 (1994).
Tanahashi, K. and Mikos, A.G., Effect of hydrophilicity and agmatine modification on degradation of poly(propylene fumarate-co-ethylene glycol) hydrogels, J. Biomed. Res. A., 67(4): 1148-1154 (2003).
Tanaka et al, Structure of FK506: a novel immunosuppressant isolated from a Streptomyces, J. Am. Chem. Soc, 109: 5031-5033 (1987).
Thomasin et al., Drug microencapsulation by PLA/PLGA coacervation in the light of thermodynamics. 1. Overview and theoretical considerations, J Pharm Sci, 87(3):259-68 (1998).
Tomalia et al., Starburst dendrimers: Molecular level control of size, shape, surface chemistry, topology and flexibility of atoms to macroscopic matter, Angewandte Chemie•International Edition in English, 29:138-175 (1990).
Visscher et al., Biodegradation of and tissue reaction to 50:50 poly(DI-lactide-co-glycolide) microcapsules, J Biomed Mater Vies. 19(3):349-65 (1985).
Wan et al., Characterization of surface property of poly(lactide-co-glycolide) after oxygen plasma treatment, Biomaterials. 25(19):4777-83 (2004).
Wang, et al., Preparation and characterization of poly(lactic-co-glycolic acid) microspheres for targeted delivery of a novel anti-cancer agent, taxol, Chem. Pharm. Bull. (Tokyo), 44(10):193540 (1996).
Wartlick et al., Highly specific HER2-mediated cellular uptake of antibody-modified nanoparticles in tumour cells, J Drug Target, 12:461-471 (2004).
Wassef et al., Liposomes as carriers for vaccines, Immunomethods, 4(3): 217-222 (1994).
Weber, A. et al., Specific interaction of IgE antibodies with a carbohydrate epitope of honey bee venom phospholipase A2, Allergy, 42(6): 464-470 (1987).
Weiss, S.J. and Halsey, J.F., A nurse with anaphylaxis to stone fruits and latex sensitivity: potential diagnostic difficulties to consider, Ann. Allergy Asthma Immunol., 77(6): 504-508 (1996).
Written Opinion for PCT/US2005/023444, 5 pages (Sep. 26, 2007).
Written Opinion for PCT/US2008/054086, 6 pages (Sep. 22, 2008).
Written Opinion for PCT/US2013/037789, 11 pages (Aug. 30, 2013).
Written Opinion for PCT/US2014/055625, 16 pages (Dec. 8, 2014).
Written Opinion for PCT/US2014/032838, 15 pages (Sep. 4, 2014).
Written Opinion for PCT/US2015/059711, 9 pages (May 12, 2016).
Yamaguchi and Anderson, In vivo biocompatibility studies of medisorb®, 65/35 D,L-lactide/glycolide copolymer microspheres, J. Controlled Ref., 24(13):81-93 (1993).
Yang et al., Plasma-treated, collagen•anchored polylactone: Its cell affinity evaluation under shear or shear-free conditions, J. Biomed Mater Res, 67A(4): 1139-47 (2003).
Yoo et al., PAMAM dendrimers as delivery agents for antisense oligonucleotides, Pharm Res, 16:1799•804 (1999).
Zheng et al., Production of microspheres with surface amino groups from blends of Poly(lactide-co-glycolide) and Poly(epsilon-CBz-L-lysine) and use for encapsulation, Biotechnology Progress, 15(4): 763-767 (1999).
Aguado et al., Controlled-release vaccines—biodegradable polylactide/polyglycolide (PL/PG) microspheres as antigen vehicles, Immunobiology, 184(2-3): 113-25 (1992).

Almería, B. et al., A multiplexed electrospray process for single-step synthesis of stabilized polymer particles for drug delivery, J. Control. Release, 154(2): 203-210 (2011).
Almería, B. et al., Controlling the morphology of electrospray-generated PLGA microparticles for drug delivery, J Colloid Interface Sci., 343(1): 125-133 (2010).
Bandyopadhyay, A. et al., The impact of nanoparticle ligand density on dendritic-cell targeted vaccines, Biomaterials, 32(11): 3094-3105 (2011).
Bramwell et al., Particulate delivery systems for biodefense subunit vaccines, Adv. Drug Deliv. Rev. 57(9): 1247-1265 (2005).
Bryniarski, K. et al., Antigen-specific, antibody-coated, exosome-like nanovesicles deliver suppressor T-cell microRNA-150 to effector T cells to inhibit contact sensitivity, J. Allergy Clin. Immunol., 132(1):170-181 (2013).
Capurso, N. A. and Fahmy, T.M, Development of a pH-responsive particulate drug delivery vehicle for localized biologic therapy in inflammatory bowel disease, Yale J. Biol. Med., 84(3): 285-288 (2011).
Capurso, N.A. et al., Development of a nanoparticulate formulation of retinoic acid that suppresses Th17 cells and upregulates regulatory T cells, Self Nonself., 1(4): 335-340 (2010).
Cartiera, M.S. et al., Partial correction of cystic fibrosis defects with PLGA nanoparticles encapsulating curcumin, Mol. Pharm., 7(1): 86-93 (2010).
Cartiera, M.S. et al., The uptake and intracellular fate of PLGA nanoparticles in epithelial cells, Biomaterials, 30(14): 2790-2798. pp. 1-22 (2009).
Corradetti, B. et al., Paracrine signalling events in embryonic stem cell renewal mediated by affinity targeted nanoparticles, Biomaterials, 33(28): 6634-6643 (2012).
Criscione J.M. et al., Self-assembly of pH-responsive fluorinated dendrimer-based particulates for drug delivery and noninvasive imaging, Biomaterials, 30(23-24): 3946-3955 (2009).
Criscione, J.M. et al., Development and application of a multimodal contrast agent for SPECT/CT hybrid imaging, Bioconjug. Chem., 22(9): 1784-1792 (2011).
Cu, Y. et al., Ligand-modified gene carriers increased uptake in target cells but reduced DNA release and transfection efficiency, Nanomedicine, 6(2): 334-343 (2010).
Demento, S. et al., Biomimetic approaches to modulating the T cell immune response with nano- and micro-particles, Conf. Proc. IEEE Eng. Med. Biol. Soc., 2009: 1161-1166 (2009).
Demento, S.L. et al., Role of sustained antigen release from nanoparticle vaccines in shaping the T cell memory phenotype, Biomaterials, 33(19):4957-4964 (2012).
Dong, H. et al., Immuno-isolation of pancreatic islet allografts using pegylated nanotherapy leads to long-term normoglycemia in full MHC mismatch recipient mice, PLoS One, 7(12): e50265 (2012).
Fadel, T.R. et al., A carbon nanotube-polymer composite for T-cell therapy, Nat Nanotechnol., 9(8): 639-647 (2014).
Fahmy, T.M. et al., A nanoscopic multivalent antigen-presenting carrier for sensitive detection and drug delivery to T cells, Nanomedicine: Nanotechnology, Biology, and Medicine, 3(1): 75-85 (2007).
Fahmy, T.M. et al., Design opportunities for actively targeted nanoparticle vaccines, Nanomedicine (Lond), 3(3): 343-355 (2008).
Fahmy, T.M. et al., Nanosystems for simultaneous imaging and drug delivery to T cells, AAPS J., 9(2): E171-180 (2007).
Florindo, H.F. et al., Surface modified polymeric nanoparticles for immunisation against equine strangles, International Journal of Pharmaceutics, 390(1): 25-31 (2010).
Gao, W. et al., Treg versus Th17 lymphocyte lineages are cross-regulated by LIF versus IL-6, Cell Cycle, 8(9):1444-1450 (2009).
Hong, E. et al., Configuration-dependent Presentation of Multivalent IL-15:IL-15Rα Enhances the Antigen-specific T Cell Response and Anti-tumor Immunity, J. Biol. Chem., 291(17): 8931-8950 (2016).
Jiang et al., Biodegradable poly(lactic-co-glycolic acid) microparticles for injectable delivery of vaccine antigens, Adv. Drug Deliv. Rev., 57(3): 391-410 (2005).

(56) References Cited

OTHER PUBLICATIONS

Keegan, M.E. et al., In vitro evaluation of biodegradable microspheres with surface-bound ligands, J. Control Release, 110(3): 574-580 (2006).
Labowsky, M. et al., An in silico analysis of nanoparticle/cell diffusive transfer: application to nano-artificial antigen-presenting cell: T-cell interaction, Nanomedicine, 11(4): 1019-1028 (2015).
Look, M. et al., Application of nanotechnologies for improved immune response against infectious diseases in the developing world, Adv. Drug Deliv. Rev., 62(4-5): 378-393 (2010).
Look, M. et al., Nanogel-based delivery of mycophenolic acid ameliorates systemic lupus erythematosus in mice, J. Clin. Invest., 123(4): 1741-1749 (2013).
Look, M. et al., The nanomaterial-dependent modulation of dendritic cells and its potential influence on therapeutic immunosuppression in lupus, Biomaterials, 35(3): 1089-1095 (2014).
McHugh, M.D. et al., Paracrine co-delivery of TGF-β and IL-2 using CD4-targeted nanoparticles for induction and maintenance of regulatory T cells, Biomaterials, 59: 172-181 (2015).
Metcalfe, S.M. and Fahmy, T.M., Targeted nanotherapy for induction of therapeutic immune responses, Trends Mol. Med., 18(2):72-80 (2012).
Mounzer, R. et al., Dynamic imaging of lymphatic vessels and lymph nodes using a bimodal nanoparticulate contrast agent, Lymphat Res. Biol., 5(3): 151-158 (2007).
Nelson, G.N. et al., Initial evaluation of the use of USPIO cell labeling and noninvasive MR monitoring of human tissue-engineered vascular grafts in vivo, FASEB J., 22(11): 3888-3895 (2008).
Ochoa, J. et al., Protective immunity of biodegradable nanoparticle-based vaccine against an experimental challenge with *Salmonella enteritidis* in mice, Vaccine, 25(22): 4410-4419 (2007).
Park, J. et al., Enhancement of surface ligand display on PLGA nanoparticles with amphiphilic ligand conjugates, J. Control Release, 156(1): 109-115 (2011).
Park, J. et al., Modulation of CD4+ T lymphocyte lineage outcomes with targeted, nanoparticle-mediated cytokine delivery, Mol. Pharm., 8(1): 143-152 (2011).
Park, J. et al., PEGylated PLGA nanoparticles for the improved delivery of doxorubicin, Nanomedicine, 5(4): 410-418 (2009).
Pochard, P. et al., Targeting Toll-like receptors on dendritic cells modifies the T(H)2 response to peanut allergens in vitro., J. Allergy Clin. Immunol. Jul. 2010;126(1): 92-7.e5 (2010).
Ragheb, R.R. et al., Induced clustered nanoconfinement of superparamagnetic iron oxide in biodegradable nanoparticles enhances transverse relaxivity for targeted theranostic, Magn. Reson. Med., 70(6): 1748-1760 (2013).
Rittchen, S., Myelin repair in vivo is increased by targeting oligodendrocyte precursor cells with nanoparticles encapsulating leukaemia inhibitory factor (LIF), Biomaterials, 56: 78-85 (2015).
Saluja, S.S., Targeting human dendritic cells via DEC-205 using PLGA nanoparticles leads to enhanced cross-presentation of a melanoma-associated antigen, Int. J. Nanomedicine, 9: 5231-5246 (2014).
Samstein, R.M. et al., The use of deoxycholic acid to enhance the oral bioavailability of biodegradable nanoparticles, Biomaterials, 29(6): 703-708 (2008).
Satterfield, B.C. et al., Tentacle probe sandwich assay in porous polymer monolith improves specificity, sensitivity and kinetics, Nucleic Acids Res., 36(19): e129 (2008).
Sehgal K et al., Nanoparticle-mediated combinatorial targeting of multiple human dendritic cell (DC) subsets leads to enhanced T cell activation via IL-15-dependent DC crosstalk, J. Immunol., 193(5): 2297-2305 (2014).
Serebrisky, D et al., CpG oligodeoxynucleotides can reverse Th2-associated allergic airway responses and alter the B7.1/B7.2 expression in a murine model of asthma, J Immunol., 165(10) :5906-5912 (2000).
Shirali, A.G. et al., Nanoparticle delivery of mycophenolic acid upregulates PD-L1 on dendritic cells to prolong murine allograft survival, Am. J. Transplant, 11(12): 2582-2592 (2011).
Siefert, A.L. et al., Artificial bacterial biomimetic nanoparticles synergize pathogen-associated molecular patterns for vaccine efficacy, Biomaterials, 97: 85-96 (2016).
Siefert, A.L. et al., Immunomodulatory nanoparticles ameliorate disease in the Leishmania (Viannia) panamensis mouse model, Biomaterials, 108: 168-176 (2016).
Srivastava, K.D. et al., Investigation of peanut oral immunotherapy with CpG/peanut nanoparticles in a murine model of peanut allergy, J. Allergy Clin. Immunol., 138(2): 536-543e4 (2016).
Steenblock, E.R. and Fahmy, T.M., A comprehensive platform for ex vivo T-cell expansion based on biodegradable polymeric artificial antigen-presenting cells, Mol Ther., 16(4): 765-772 (2008).
Stern, E. et al., Spatiotemporal control over molecular delivery and cellular encapsulation from electropolymerized micro- and nanopatterned surfaces, Adv Funct Mater., 19(18):2888-2895 (2009).
Strohbehn G et al., Imaging the delivery of brain-penetrating PLGA nanoparticles in the brain using magnetic resonance, J. Neurooncol, 121(3): 441-449 (2015).
Vacic, A., Determination of molecular configuration by debye length modulation, J Am Chem Soc., 133(35): 13886-13889 (2011).
Zhao, J.W. et al., Modelling of a targeted nanotherapeutic 'stroma' to deliver the cytokine LIF or XAV939, a potent inhibitor of Wnt-β-catenin signalling, for use in human fetal dopaminergic grafts in Parkinson's disease, Dis. Model Mech., 7(10): 1193-1203 (2014).

\* cited by examiner

NANOPARTICLES FOR TREATMENT OF ALLERGY

RELATED APPLICATIONS

This application claims priority under 35 U.S.C §119(e) to U.S. provisional patent application, U.S. Ser. No. 61/636,921, filed Apr. 23, 2012, and is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 18, 2015, is named "2006517-0209_SL.txt" and is 519 bytes in size.

BACKGROUND

Allergic reactions pose serious public health problems worldwide. Pollen allergy alone (allergic rhinitis or hay fever) affects about 10-15% of the population, and generates huge economic costs. For example, reports estimate that pollen allergy generated $1.8 billion of direct and indirect expenses in the United States in 1990 (*Fact Sheet*, National Institute of Allergy and Infectious Diseases; McMenamin, *Annals of Allergy* 73:35, 1994). Asthma, which can be triggered by exposure to antigens, is also a serious public health problem, and like anaphylactic allergic reactions, can lead to death in extreme cases. Asthma currently accounts for millions of visits yearly to hospitals and is increasing in frequency. The only treatment currently available is for alleviation of symptoms, for example, to relieve constriction of airways.

Perhaps even more serious than the economic costs associated with pollen and other inhaled allergens (e.g., molds, dust mites, animal danders) is the risk of an anaphylactic allergic reaction observed with certain allergens, such as food allergens, insect venoms, drugs, and latex.

SUMMARY

The present invention encompasses the surprising finding that certain nanoparticle compositions can have beneficial effects on allergy. Particularly surprising is the provided finding that certain nanoparticle compositions can have such effects even when prepared without a known allergy-specific therapeutic.

The present invention provides nanoparticle compositions useful in the treatment of allergy. In some embodiments, such nanoparticle compositions comprise individual polymer particles, in many embodiments further containing one or more moieties that, for example, target relevant polymer particles to one or more particular tissues and/or impart to the relevant particles one or more attributes (e.g., immunological attributes) of a bacterial cell. In some embodiments, such moieties are partially or completely surface-associated (i.e., associated with the surface of nanoparticles).

For example, in some embodiments, moieties that mimic microbial (e.g., bacterial) cell characteristics or features are or comprise entities known as pathogen-associated molecular patterns ("PAMPs"). In general, PAMPs are entities that are associated with bacterial cells and are recognized by immune system cells in an organism into which the bacterial cells are introduced. In some embodiments, PAMPs are recognized by Toll-like receptors ("TLRs") and/or other pattern recognition receptors ("PRRs"). In some embodiments, PAMPs are recognized by plant and/or animal TLRs and/or PRPs.

In some embodiments, PAMPs are or comprise entities associated with the outer surface of a bacterial cell, including, but not limited to, membrane-associated proteins and/or peptides, receptors embedded in bacterial membranes, etc. Exemplary PAMPs include, but are not limited to, bacterial lipopolysaccharide ("LPS"), bacterial flagellin, lipoteichoic acid from gram positive bacteria, diacyl lipopeptides, triacyl lipopeptides, lipopeptide Pam3Cys-SK4 ("Pam"), zymosan from yeast cell wall, peptidoglycans, double-stranded RNAs ("dsRNAs"), unmethylated CpG motifs, heat shock proteins (e.g., heat shock protein 60, "Hsp60"), taxol, viral double-stranded RNA (dsRNA), viral single-stranded RNA (ss-RNA), double-stranded DNA (dsDNA), haemozoin, characteristic portions thereof, and/or combinations thereof.

In some embodiments, individual nanoparticles in a nanoparticle composition comprise at least 1, at least 2, at least 3, at least 4, at least 5, at least 6, at least 7, at least 8, at least 9, or at least 10 different functional elements (e.g., microbial mimic entities). In some embodiments, individual nanoparticles in a nanoparticle composition do not comprise any functional elements (e.g., microbial mimic entities). In some embodiments, a provided nanoparticle composition comprises a plurality of distinct sets of nanoparticles, each of which comprises a different set of functional elements (e.g., microbial mimic entities).

One aspect of the present invention encompasses the insight that desirable nanoparticle compositions for use in accordance with the present invention may be prepared from or similarly to certain known nanoparticle compositions developed for the treatment of allergy, except that at least one component considered to be essential for therapeutic activity of those compositions with respect to allergy is not included. In particular, in some embodiments, provided nanoparticle compositions lack an allergy-specific therapeutic agent. For example, in some embodiments, provided nanoparticle compositions do not include an allergen.

Prior art modular nanoparticle compositions have been described as useful vaccines, for example, in U.S. Ser. No. 12/527,143 (the '143 application) and PCT/US2008/054086 (the '086 application), published as US 2010/0104503 and WO2008/115641, respectively (collectively, the "Mellman Applications"); and/or in PCT/US2009/049431 (the '431 application) and U.S. Ser. No. 12/075,667 (the '667 application), published as WO2010/003009 and US 2009/0011993, respectively, (collectively, the "Emory Applications"), and references cited therein, including, but not limited to, U.S. Ser. No. 10/542,185 (the '185 application), U.S. Ser. No. 11/430,091 (the '091 application), U.S. Ser. No. 11/411,193 (the '193 application), U.S. Ser. No. 08/613,830 (the '830 application), U.S. Ser. No. 10/215,306 (the '306 application), and PCT/US2005/016912 (the '912 application), published as US 2007/0148074, US 2007/0092575, US 2006/0246139, U.S. Pat. No. 5,753,234, U.S. Pat. No. 7,081,489, and WO 06/052285, respectively; all of the foregoing of which are incorporated herein by reference in their entirety. As described, these vaccine compositions include 1) an antigen that is incorporated or encapsulated in 2) a polymeric nanoparticle; and 3) one or more adaptor elements that modularly couple to the nanoparticle compositions functional elements that impart useful functions to the nanoparticle compositions. Exemplary functional elements are said to include, for example, targeting moieties (e.g., dendritic cell targeting moieties, epithelial cell targeting moieties, etc.), entities that protect one or more aspects of the composition from degradation, endosome-disrupting agents, etc. Further optional components include, for example, adjuvants, contrast agents and other markers, etc.

The present invention encompasses the surprising insight that prior art modular nanoparticle compositions, such as those described in the Mellman Applications, Emory Applications, and/or references cited therein, can act as effective vaccine compositions even though an element previously considered to be essential—the antigen itself—is not included! The present invention further encompasses the finding that useful allergy vaccine compositions can be prepared from nanoparticle compositions that substantially lack any allergy-specific antigen, but include one or more components or features that is reminiscent of a microbial cell and/or that otherwise targets, activates, or stimulates one or more immune system components typically involved in responding to microbial infection.

In some embodiments, the present invention provides nanoparticle compositions that substantially lack an allergy-specific antigen and include one or more PAMPs, either on their surface, encapsulated internally, or both.

In some embodiments, provided nanoparticle compositions are combined with pharmaceutically acceptable excipients to provide pharmaceutical formulations. The present invention provides pharmaceutical compositions for use in medicine, for example in treatment, prevention, and/or diagnosis of allergy.

Provided nanoparticle compositions may be used in accordance with the present invention in any of a variety of therapeutic, prophylactic, and/or diagnostic contexts. In some embodiments, the present invention provides uses that involve administration of a composition (e.g., a pharmaceutical composition) comprising a provided nanoparticle composition to a subject suffering from or susceptible to allergy (e.g., to an allergic response to one or more particular antigens). In some embodiments, such administration partially or completely treats, alleviates, ameliorates, relives, inhibits, delays onset of, reduces severity of and/or reduces incidence of one or more symptoms of allergy. In some embodiments, a therapeutically effective amount is an amount sufficient to achieve one or more particular biological effects, including, but not limited to, (i) alleviating one or more symptoms of allergy; (ii) reducing the amount of IgE antibodies in an individual; (iii) preventing reemergence, reducing the likelihood of reemergence, and/or delaying the reemergence of one or more symptoms of allergy; and/or (iv) preventing, reducing the likelihood of, and/or delaying the onset of an increase in the number of circulating IgE antibodies in an individual. In some embodiments, pharmaceutical compositions comprising one or more empty nanoparticles may be used to prevent, reduce the recurrence of, and/or delay the onset of allergy. In some embodiments, use of provided compositions affects a subject's allergy to a particular antigen; in some embodiments, use of provided compositions affects a subject's allergy to a plurality (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, etc.) of distinct antigens. In some embodiments, provided compositions have pan-allergic effects.

That is, in some embodiments, the present invention encompasses the recognition that provided nanoparticle compositions may be useful for treating and/or preventing a single allergy. In some embodiments, the present invention encompasses the recognition that provided nanoparticle compositions may be useful for treating and/or preventing multiple different allergies. In some embodiments, the present invention encompasses the recognition that provided nanoparticle compositions may be useful for treating and/or preventing multiple different allergies in a single patient. For example, subjects suffering from and/or susceptible to allergy are frequently allergic to more than one allergen, e.g., at least 1, at least 2, at least 3, at least 4, at least 5, at least 6, at least 7, at least 8, at least 9, at least 10, at least 15, at least 20, at least 25, or more different allergens. Thus, in some embodiments, an provided nanoparticle composition may be used for treating and/or preventing at least 1, at least 2, at least 3, at least 4, at least 5, at least 6, at least 7, at least 8, at least 9, at least 10, at least 15, at least 20, at least 25, or more different allergies in a single patient. In some embodiments, an provided nanoparticle composition is administered to a subject suffering from and/or susceptible to multiple different allergies, e.g., at least 1, at least 2, at least 3, at least 4, at least 5, at least 6, at least 7, at least 8, at least 9, at least 10, at least 15, at least 20, at least 25, or more different allergies, such that the subject's symptoms are reduced and/or improved. In some embodiments, an provided nanoparticle composition is administered to a subject suffering from and/or susceptible to multiple different allergies, e.g., at least 1, at least 2, at least 3, at least 4, at least 5, at least 6, at least 7, at least 8, at least 9, at least 10, at least 15, at least 20, at least 25, or more different allergies, such that onset of the subject's symptoms is delayed. In some embodiments, provided nanoparticle compositions effectively treat and/or prevent all of a subject's allergies. In some embodiments, provided nanoparticle compositions effectively treat and/or prevent substantially all of a subject's allergies. In some embodiments, provided nanoparticle compositions are useful as a "pan-allergy" treatment, meaning that provided nanoparticle compositions are useful for treatment and/or prevention of all of a subject's allergies. Without wishing to be bound by any one particular theory, provided nanoparticle compositions may function to suppress and/or decrease a subject's $T_H2$-type responses and/or enhance and/or increase a subject's $T_H1$-type responses.

The invention also provides pharmaceutical compositions comprising therapeutically effective amounts of provided nanoparticles for use in combination with at least one other therapeutic agent. In some embodiments, the other therapeutic agent is selected from the group consisting of anti-histamines, glucocorticoids; epinephrine (adrenaline); theophylline; cromolyn sodium; anti-leukotrienes; Montelukast) (SINGULAIR®; Zafirlukast (ACCOLATE®); anti-cholinergics; decongestants; mast cell stabilizers; immunotherapy (progressively larger doses of a specific allergen); monoclonal anti-IgE antibodies (e.g., omalizumab); and/or combinations thereof.

DEFINITIONS

Adaptor elements: As used herein, the term "adaptor elements" refers to molecular entities that associate with polymeric nanoparticles such as those described in the Mellman Applications, Emory Applications, and/or references cited therein and provide substrates that facilitate the modular assembly and disassembly of functional elements onto the nanoparticles. Adaptor elements can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Adaptor elements can also be covalently coupled to functional elements in the absence of affinity tags.

Administration: As used herein, the term "administration" refers to the administration of a provided nanoparticle composition to a subject. Unless otherwise indicated, administration is not limited to any particular route but rather can refer to any route accepted as appropriate by the medical community. For example, the present invention contemplates routes of administering that include, but are not limited to, oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, powders, ointments, liniments, gels, drops, etc.), mucosal, intranasal, buccal, enteral, vitreal, and/or sublingual administration; by intratracheal instillation, bronchial instillation, and/or inhalation; as an oral spray, nasal spray, and/or aerosol, and/or through a portal vein catheter; and/or combinations of any of the foregoing. In some embodiments of the present invention, administration is oral, intragastric, mucosal, intranasal, buccal, enteral, and/or sublingual. In some embodiments of the present invention, administration is oral.

Affinity tag: The term "affinity tag" is used herein to refer to molecular entities that form highly specific, non-covalent, physiochemical interactions with defined binding partners, which are referred to as "complementary" affinity tags. In some embodiments, affinity tags are associated with polymer nanoparticles such as those described in the Mellman Applications, Emory Applications, and/or references cited therein.

Antigen: The term "antigen", as used herein, refers to an entity that elicits production of an antibody (i.e., a humoral response) and/or an antigen-specific reaction with T-cells (i.e., a cellular response) in an animal.

Allergen: The term "allergen", as used herein, refers to a subset of antigens which elicit the production of antibodies, including IgE, IgA, IgM, IgG, IgD, etc. In general, an "allergen" is an antigen that elicits an allergic immune response in a subject. In some embodiments, an allergen is an antigen that is statistically correlated with immune responses in a population of subjects. In some embodiments, allergens are protein allergens.

Allergic reaction: The phrase "allergic reaction," as used herein, refers to an immune response that is IgE mediated with clinical symptoms primarily involving the cutaneous (e.g., uticana, angiodema, pruritus), respiratory (e.g., wheezing, coughing, laryngeal edema, rhinorrhea, watery/itching eyes), gastrointestinal (e.g., vomiting, abdominal pain, diarrhea), and cardiovascular (e.g., if a systemic reaction occurs) systems. In some embodiments, an asthmatic reaction is considered to be a form of allergic reaction.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. Amino acids, including carboxy- and/or amino-terminal amino acids in peptides, can be modified by methylation, amidation, acetylation, and/or substitution with other chemical groups that can change the peptide's circulating half-life without adversely affecting their activity. Amino acids may participate in a disulfide bond. In some embodiments, the term "amino acid" is used to refer to a free amino acid; in some embodiments, the term "amino acid" refers to an amino acid residue of a polypeptide.

Anaphylactic allergen: The phrase "anaphylactic allergen," as used herein, refers to a subset of allergens that are recognized to present a risk of anaphylactic reaction in allergic individuals (e.g., that show a statistically significant correlation with the incidence of anaphylactic reactions) when encountered in their natural state, under natural conditions. For example, pollen allergens, mite allergens, allergens in animal danders or excretions (e.g., saliva, urine), and fungi allergens are typically not considered to be anaphylactic allergens. On the other hand, food allergens, insect allergens, and rubber allergens (e.g., from latex) are generally considered to be anaphylactic allergens. In some embodiments, anaphylactic allergens comprise food allergens, including, but not limited to, nut allergens (e.g., from peanut, walnut, almond, pecan, cashew, hazelnut, pistachio, pine nut, brazil nut), dairy allergens (e.g., from egg, milk), seed allergens (e.g., from sesame, poppy, mustard), soybean, wheat, and fish allergens (e.g., from shrimp, crab, lobster, clams, mussels, oysters, scallops, crayfish). Some anaphylactic allergens correlate with incidence of anaphylactic reactions so severe as to create a risk of death.

Anaphylaxis or anaphylactic reaction: The phrase "anaphylaxis" or "anaphylactic reaction," as used herein, refers to a subset of allergic reactions characterized by mast cell degranulation secondary to cross-linking of the high-affinity IgE receptor on mast cells and basophils induced by an anaphylactic allergen with subsequent mediator release and the production of severe systemic pathological responses in target organs, e.g., airway, skin digestive tract, and cardiovascular system. As is known in the art, the severity of an anaphylactic reaction may be monitored, for example, by assaying cutaneous reactions, puffiness around the eyes and mouth, vomiting, and/or diarrhea, followed by respiratory reactions such as wheezing and labored respiration. The most severe anaphylactic reactions can result in loss of consciousness and/or death.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, an animal is suffering from and/or is susceptible to allergy. In some embodiments, an animal may be a transgenic animal, genetically engineered animal, and/or a clone.

Antibody: As used herein, the term "antibody" refers to any immunoglobulin, whether natural or wholly or partially synthetically produced. All derivatives thereof which maintain specific binding ability are also included in the term. In some embodiments, the term "antibody" refers to any protein having a binding domain which is homologous or largely homologous to an immunoglobulin-binding domain.

Antibody proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. In certain embodiments, an antibody may be a member of the IgG immunoglobulin class. As used herein, the term "antibody fragment" refers to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids. In some embodiments, an antibody may be a human antibody. In some embodiments, an antibody may be a humanized antibody.

Antigen presenting cell: The phrase "antigen presenting cell" or "APC," as used herein, refers to cells which process and present antigens to T-cells to elicit an antigen-specific response, e.g., macrophages and dendritic cells.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the term a "characteristic portion" of a substance, in the broadest sense, is one that shares a degree of sequence or structural identity with respect to the whole substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide, in that they can be used to distinguish the protein or polypeptide from other proteins or polypeptides and/or to define a particular protein or polypeptide as a member of a particular family or class of proteins or polypeptides (e.g., different from other families or classes of proteins or polypeptides). In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Decreased anaphylactic reaction: The phrase "decreased anaphylactic reaction," as used herein, relates to a decrease in one or more clinical symptoms following treatment of symptoms associated with exposure to an anaphylactic allergen, which can involve exposure via cutaneous, respiratory, gastrointestinal, and mucosal (e.g., ocular, nasal, aural, rectal, vaginal, buccal, sublingual, etc.) surfaces or a subcutaneous injection (e.g., via a bee sting). In some embodiments, an anaphylactic reaction is considered to be "decreased" when clinical symptoms are at least 10%, at least 20%, at least 30%, at least 40%, at least 50%, at least 60%, at least 70%, at least 80%, at least 90%, at least 95%, or at least 99% improved.

Empty nanoparticle composition: The term "empty nanoparticle composition," as used herein, refers to a nanoparticle composition which does not include a known allergy-specific therapeutic (e.g., a specific allergic antigen).

Encapsulated: The term "encapsulated" (also "encapsulate" or "encapsulating") is used herein to mean that the encapsulated entity is completely surrounded by another material. In some embodiments, an encapsulated entity is not exposed to other agents that are present outside the encapsulating material, when capsules of the encapsulating material (containing encapsulated entity) are combined with the other agents (e.g., in a mixture or solution).

Endosome-disrupting agent: The term "endosome-disrupting agent" is used herein to refer to entities that cause disruption of endosomal membranes, for example during endocytosis. Endosome-disrupting agents can facilitate transit of extracellular antigens into the cytoplasm of antigen-presenting cells, and therefore can facilitate processing of the antigens for presentation with MHC molecules (e.g., MHC class I molecules) at the surface of the antigen presenting cells.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized.

Functional elements: The term "functional elements" is used herein as it to refer to molecular entities that associate with polymer nanoparticles such as those described in the Mellman Applications, Emory Applications, and/or references cited therein and impart a particular function to the nanoparticles. Functional elements can associate with nanoparticles through adaptor elements, or through direct association with the nanoparticle surface. Functional elements can be conjugated to affinity tags, which form highly specific, non-covalent, physiochemical interactions with complementary affinity tags conjugated to adaptor elements.

Thus, functional elements can be coupled to adaptor elements non-covalently through affinity tags. Alternatively or additionally, functional elements can be covalently coupled to adaptor elements in the absence of affinity tags. Functional elements can also be covalently or non-covalently associated with the surface of nanoparticles without the use of adaptor elements.

Gene: As used herein, the term "gene" has its meaning as understood in the art. It will be appreciated by those of ordinary skill in the art that, in some embodiments, the term "gene" may refer to a nucleic acid that includes gene regulatory sequences (e.g., promoters, enhancers, etc.) and/or intron sequences; in some embodiments, the term "gene" may refer to a nucleic acid that includes coding sequences (e.g., for a polypeptide or functional RNA (e.g., tRNA, siRNA, miRNA, etc.). For purposes of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Micelle: As used herein, the term "micelle" refers to an entity comprising a boundary and a lumen. In some embodiments, a micelle is an entity that forms in an aqueous context. In some embodiments, a micelle comprises one or more amphiphilic entities, detergents, surfactants, lipids, and/or combinations thereof. In some embodiments, a micelle does not contain an amphiphilic entity. In some embodiments, a micelle does not contain a detergent. In some embodiments, a micelle does not contain a surfactant. In some embodiments, a micelle does not contain a lipid.

In some embodiments, nanoparticles are micelles in that they comprise an enclosed compartment, separated from the bulk solution by a micellar membrane. A "micellar membrane" comprises entities which surround and enclose a space or compartment (e.g., to define a lumen).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Known allergy therapeutic: As used herein, the term "known allergy therapeutic" describes a biologically active agent known to be useful for treatment of allergy. Exemplary known allergy therapeutics include, but are not limited to, any of the therapeutics described in U.S. Pat. Nos. 5,558,869, 5,973,121, 6,835,824, 6,486,311, and/or 7,485,708, and/or in US Patent Publication Numbers 2003/0035810, 2003/0202980, 2004/0208894, 2004/0234548, 2007/0213507, 2010/0166802, and/or 2011/0027298, all of which are incorporated herein by reference; antihistamines glucocorticoids; epinephrine (adrenaline); theophylline; cromolyn sodium; anti-leukotrienes; Montelukast (SINGULAIR®); Zafirlukast (ACCOLATE®); anti-cholinergics; decongestants; mast cell stabilizers; immunotherapy (progressively larger doses of a specific allergen); monoclonal anti-IgE antibodies (e.g., omalizumab); and/or combinations thereof.

Nanoemulsion: An emulsion is traditionally defined in the art "as a system . . . consisting of a liquid dispersed with or without an emulsifier in an immiscible liquid usually in droplets of larger than colloidal size" *Medline Plus Online Medical Dictionary, Merriam Webster* (2005). The term "nanoemulsion," as used herein, refers to an emulsion in which at least some of the droplets (or particles) have diameters in the nanometer size range. As will be understood by those of ordinary skill in the art, a nanoemulsion is characterized by droplets or particles one thousand fold smaller than microemulsion droplets or particles.

Nanoparticle: As used herein, the term "nanoparticle" refers to any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane. A "micellar membrane" comprises entities which surround and enclose a space or compartment (e.g., to define a lumen).

Nanoparticle composition: As used herein, the term "nanoparticle composition" refers to any composition that contains at least one nanoparticle. In some embodiments, a nanoparticle composition includes a uniform collection of nanoparticles. In some embodiments, a nanoparticle composition contains a defined distribution of nanoparticles of particular sizes and/or features (e.g., structural and/or functional features)

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which an provided nanoparticle composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Provided Composition: As used herein, a "provided composition" refers to any composition described herein, including, but not limited to, provided nanoparticle compositions. In some embodiments, provided compositions include provided nanoparticle compositions comprising one or more functional elements (e.g., microbial mimic entities) and/or substantially lacking allergy-specific agents.

Refractory: The term "refractory" as used herein, refers to any subject that does not respond with an expected clinical efficacy following the administration of provided nanoparticle compositions as normally observed by practicing medical personnel.

Small Molecule: In general, a "small molecule" is a molecule that is less than about 5 kilodaltons (kD) in size.

In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., allergy) has been diagnosed with and/or exhibits one or more symptoms of the disease, disorder, or condition. In some embodiments, an individual who is suffering from allergy does not display any symptoms of allergy and/or has not been diagnosed with allergy. In some embodiments, an individual who is suffering from allergy is an individual who has one or more IgE antibodies (e.g., allergen-specific IgE antibodies) in his/her blood. In some embodiments, an individual is considered to be suffering from allergy to a particular antigen if that person shows a prick skin test mean wheal diameter at least 1 mm, at least 2 mm, at least 3 mm, at least 4 mm, or at least 5 mm greater than the negative control after allergen exposure (e.g., within 5 minutes, within 10 minutes, within 15 minutes, within 30 minutes, within 1 hour, within 2 hours, within 3 hours, within 4 hours, or within 5 hours of allergen exposure). In some embodiments, an individual is considered to be suffering from allergy to a particular antigen if that person shows an allergen-specific IgE level of at least 0.1 $kU_A/L$, at least 0.15 $kU_A/L$, at least 0.2 $kU_A/L$, at least 0.25 $kU_A/L$, at least 0.3 $kU_A/L$, at least 0.35 $kU_A/L$, at least 0.4 $kU_A/L$, at least 0.45 $kU_A/L$, at least 0.5 $kU_A/L$, at least 0.6 $kU_A/L$, at least 0.7 $kU_A/L$, at least 0.8 $kU_A/L$, at least 0.9 $kU_A/L$, or at least 1.0 $kU_A/L$ after allergen exposure (e.g., within 5 minutes, within 10 minutes, within 15 minutes, within 30 minutes, within 1 hour, within 2 hours, within 3 hours, within 4 hours, or within 5 hours of allergen exposure). In some embodiments, an individual is considered to be suffering from allergy to a particular antigen if that person presents and/or has a history of an immediate hypersensitivity reaction. In some embodiments, an immediate hypersensitivity reaction includes one or more of the following after allergen exposure (e.g., within 5 minutes, within 10 minutes, within 15 minutes, within 30 minutes, within 1 hour, within 2 hours, within 3 hours, within 4 hours, or within 5 hours of allergen exposure): generalized urticaria, generalized flushing, nasal congestion, rhinorrhea, sneezing, shortness of breath, wheezing, nausea, abdominal pain, vomiting, hypotension, and/or combinations thereof.

Surface moiety: As used herein, a "surface moiety" refers to an entity which, when associated with a nanoparticle, is partly or wholly located on the surface of the nanoparticle. In some embodiments, an entity is considered to be on the surface of a nanoparticle if its presence is detected when the nanoparticle is contacted with a detection system under conditions that preserve structural integrity of the nanoparticle.

Microbial mimic entities: A "microbial mimic" entity, as that term is used herein, is an entity whose present in or on nanoparticles in a nanoparticle composition as described herein imparts on the nanoparticle one or more features of characteristics of microbial cells, such as bacterial cells. In some embodiments, microbial mimic entities are or comprise entities that can be found in nature associated with the outer surface of a bacterial cell. For example, in some embodiments, microbial mimic entities may be or include one or more membrane-associated proteins and/or peptides, receptors embedded in bacterial membranes, etc. In some embodiments, exemplary microbial mimic entities include, but are not limited to, bacterial lipopolysaccharide ("LPS"), bacterial flagellin, lipoteichoic acid from gram positive bacteria, peptidoglycan, double-stranded RNAs ("dsRNAs"), unmethylated CpG motifs, characteristic portions thereof, and/or combinations thereof. In some embodiments, one or more microbial mimic entities are associated with surfaces of nanoparticles in provided nanoparticle compositions. In some embodiments, one or more microbial mimic entities are encapsulated within nanoparticles in provided nanoparticle compositions. In some embodiments, one or more particular microbial mimic entities is/are both associated with surfaces of and encapsulated within nanoparticles in provided nanoparticle compositions.

Susceptible to: An individual who is "susceptible to" a disease, disorder, or condition (e.g., allergy) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition and/or carries one or more genetic elements whose presence in a genome correlates with increased incidence of the disease, disorder, or condition. In some embodiments, a risk of developing a disease, disorder, and/or condition is a population-based risk (e.g., family members of individuals suffering from allergy, etc.). In some embodiments, an individual can be considered susceptible to allergy without having suffered a reaction to the particular allergen in question. For example, if the individual has suffered an allergic or anaphylactic reaction to a related allergen (e.g., one from the same source or one for which shared allergies are common), that individual may be considered susceptible to anaphylactic reaction to the relevant allergen. Similarly, if members of an individual's family react to a particular allergen, the individual may be considered to be susceptible to anaphylactic reaction to that allergen.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. To give but a few examples, exemplary symptoms of allergy include, but are not limited to, anaphylaxis (which frequently involves severe systemic pathological responses in target organs, e.g., airway, skin digestive tract, and cardiovascular system), cutaneous symptoms (e.g., uticana, angiodema, pruritus, puffiness around the eyes and mouth), respiratory symptoms (e.g., wheezing, labored respiration, coughing, laryngeal edema, rhinorrhea, watery/itching eyes), gastrointestinal symptoms (e.g., vomiting, abdominal pain, diarrhea), cardiovascular symptoms (e.g., if a systemic reaction occurs), asthma, and/or combinations thereof. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that has a therapeutic effect and/or elicits a desired therapeutic effect, when administered to a subject.

Therapeutically effective amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition (e.g., allergy). In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. In some embodiments, reference to a therapeutically effective amount may be a reference to an amount as measured in one or more specific tissues. Those of ordinary skill in the art will appreciate that, in some embodiments, a therapeutically effective amount may be formulated and/or administered in a single dose. In some embodiments, a therapeutically effective agent may be formulated and/or administered in a plurality of doses, for example, as part of a dosing regimen. In some embodiments, a unit dose that contains a dose to be administered as part of a therapeutically effective regimen is referred to as containing a "therapeutically effective" amount even though administration of only that single unit dose might not be expected to correlate with therapeutic effectiveness (e.g., across a population).

Treatment: As used herein, the term "treatment" (also "treat" or "treating") refers to any administration of a substance (e.g., provided nanoparticle compositions) that partially or completely alleviates, ameliorates, relives, inhibits, delays onset of, reduces severity of, and/or reduces incidence of one or more symptoms, features, and/or causes of a particular disease, disorder, and/or condition (e.g., allergy). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DESCRIPTION OF CERTAIN EMBODIMENTS

The present invention encompasses the surprising finding that nanoparticle compositions can have beneficial effects on allergy even when prepared without a known allergy-specific therapeutic (e.g., without a particular antigen). In some embodiments, such provided nanoparticle compositions are associated with or otherwise include one or more "PAMPs" ("pathogen-associated molecular patterns"), such that the nanoparticles mimic bacterial cells. In some embodiments, some or all of such PAMPs are present on surfaces of nanoparticles in provided nanoparticle compositions.

The present invention provides various compositions and methods relating to provided nanoparticle compositions. For example, in some embodiments, the present invention encompasses the surprising finding that provided nanoparticles may be useful for treatment and/or prevention of multiple different allergies in a single patient. The present invention encompasses the recognition that provided nanoparticles may be useful as a "pan-allergy" therapeutic and/or vaccine.

Allergy

Allergic reactions result when an individual's immune system overreacts, or reacts inappropriately, to an encountered antigen. Typically, there is no allergic reaction the first time an individual is exposed to a particular antigen. However, it is the initial response to an antigen that primes the system for subsequent allergic reactions. In particular, the antigen is taken up by antigen presenting cells ("APCs") (e.g., macrophages and dendritic cells) that degrade the antigen and then display antigen fragments to T cells. T cells, in particular $CD4^+$"helper" T-cells, respond by secreting a collection of cytokines that have effects on other immune system cells. The profile of cytokines secreted by responding $CD4^+$ T cells determines whether subsequent exposures to the antigen will induce allergic reactions. Two classes of $CD4^+$ T cells (Th1 and Th2) influence the type of immune response that is mounted against an antigen.

Th2 cells can secrete a variety of cytokines and interleukins including IL-4, IL-5, IL-6, IL-10 and IL-13. One effect of IL-4 is to stimulate the maturation of B cells that produce IgE antibodies specific for the antigen. Allergic responses to allergens are characterized by the production of antigen-specific IgE antibodies which are dependent on help from IL-4 secreting $CD4^+$ T cells. These antigen-specific IgE antibodies attach to receptors on the surface of mast cells, basophils and eosinophils, where they act as a trigger to initiate a rapid allergic reaction upon the next exposure to antigen. When the individual encounters the antigen a second time, the antigen is quickly bound by these surface-associated IgE molecules. Each antigen typically has more than one IgE binding site, so that the surface-bound IgE molecules quickly become crosslinked to one another through their simultaneous (direct or indirect) associations with antigen. Such cross-linking induces mast cell degranulation, resulting in the release of histamines and other substances that trigger allergic reactions. Individuals with high levels of IgE antibodies are known to be particularly prone to allergies.

Nanoparticles

In general, a nanoparticle composition is any composition that includes at least one nanoparticle. The present invention encompasses the remarkable observation that nanoparticle compositions can act as effective allergy vaccines even when the compositions do not include any allergy-specific therapeutic components. For example, the present invention provides the specific insight that useful allergy vaccines can be prepared from nanoparticle compositions that lack allergy-specific antigens.

In general, a nanoparticle is or comprises any particle having a diameter (e.g., average diameter) of less than 1000 nanometers (nm). In some embodiments, provided nanoparticle compositions comprise a population of nanoparticles. In some embodiments, a population of nanoparticles comprises nanoparticles of a uniform size. In some embodiments, a population of nanoparticles comprises nanoparticles of different sizes; in some embodiments showing a particular size distribution. In many embodiments, provided nanoparticle compositions comprise nanoparticles having sizes (e.g., average sizes) within a range defined by a lower limit and an upper limit. In some embodiments, the lower limit is 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, or more. In some embodiments, the upper limit is 1000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm or less. In some embodiments, provided nanoparticle compositions comprise nanoparticles having sizes (e.g., average sizes) similar to the size of bacterial cells. For example, in some embodiments, provided nanoparticle compositions comprise nanoparticles having sizes (e.g., average sizes) ranging between 100 nm and 2000 nm, between 100 nm and 1000 nm, between 100 nm and about 500 nm, between 100 nm and about 300 nm, or between 100 nm and about 200 nm.

In some embodiments, provided nanoparticle compositions are substantially free of particles larger than about 2000 nm, about 1000 nm, about 900 nm, about 800 nm, about 700 nm, about 600 nm, about 500 nm, about 400 nm, or about 300 nm. In some embodiments, provided nanoparticle compositions comprise no more than about 50%, about 25%, about 10%, about 5%, or about 1% of particles larger than about 2000 nm, about 1000 nm, about 900 nm, about 800 nm, about 700 nm, about 600 nm, about 500 nm, about 400 nm, or about 300 nm.

In some embodiments, nanoparticles are micelles in that they comprise an enclosed compartment, separated from the bulk solution by a micellar membrane. A "micellar membrane" comprises entities which surround and enclose a space or compartment (e.g., to define a lumen). In some embodiments, nanoparticles are solid in that they do not comprise an enclosed compartment.

In some embodiments, provided nanoparticles comprise and/or are formed from at least one polymer, including, but not limited to, a homopolymer, diblock triblock, multibock copolymer, linear polymer, dendritic polymer, branched polymer, random block, etc. In some embodiments, provided nanoparticle compositions comprise a polymer that is biocompatible and/or biodegradable. In some embodiments, provided nanoparticle compositions comprise a polymer that is biologically degradable, chemically degradable, or both biologically and chemically degradable. In some embodiments, provided nanoparticle compositions comprise poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), poly(anhydrides), PEGylated poly(anhydrides), poly(ortho esters) derivatives of poly(ortho esters), PEGylated poly(ortho esters), poly(caprolactones), derivatives of poly(caprolactone), PEGylated poly(caprolactones), polylysine, derivatives of polylysine, PEGylated polylysine, poly(ethylene imine), derivatives of poly(ethylene imine), PEGylated poly(ethylene imine), poly(acrylic acid), derivatives of poly(acrylic acid), PEGylated poly(acrylic acid), poly(urethane), PEGylated poly(urethane), derivatives of poly(urethane), poly(lactide), poly(glycolide), poly(lactic co-glycolic acid), poly(arylates), poly(anhydrides), poly(hydroxy acids), polyesters, poly(ortho esters), polycarbonates, poly(propylene fumarates), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), polycyanoacrylates, polyalkylene oxalates, polyalkylene succinates, poly(malic acid), poly(methyl vinyl ether), poly(ethylene imine), poly(acrylic acid), poly(maleic anhydride), polyurethanes, polysaccharides, and/or combinations thereof. In some embodiments, provided nanoparticle compositions comprise a blend and/or mixture of polymers.

In some embodiments, provided nanoparticle compositions comprise a synthetic polymer. Exemplary synthetic polymers include, but are not limited to, polyanhydrides, polyhydroxyacids (e.g., polylactic acid, polyglycolic acid, copolymers of polylactic acid, copolymers of polyglycolic acid, etc.), polyesters, polyamides, polyorthoesters, polyphosphazenes, and/or combinations thereof. In some embodiments, provided nanoparticle compositions comprise a natural polymer. Exemplary naturally occurring polymers include, but are not limited to, proteins, polysaccharides (e.g., collagen, hyaluronic acid, albumin, starch, cellulose, gelatin, etc.), and/or combinations thereof.

In some embodiments, provided nanoparticle compositions comprise one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and/or combinations thereof.

In some embodiments, provided nanoparticle compositions do not comprise a polymeric component. In some embodiments, provided nanoparticle compositions comprise one or more of metal particles, quantum dots, ceramic particles, bone particles, viral particles, and/or combinations thereof. In some embodiments, a provided nanoparticle composition is an aggregate of non-polymeric components, such as an aggregate of metal atoms (e.g. gold atoms).

In some embodiments, provided nanoparticle compositions comprise quantum dots (QDs). QDs are bright, fluorescent nanocrystals with physical dimensions small enough such that the effect of quantum confinement gives rise to unique optical and electronic properties (see, e.g., U.S. Pat. Nos. 6,322,901; 6,576,291; and 6,815,064; all of which are incorporated herein by reference). In some embodiments, QDs are rendered water soluble by applying coating layers comprising a variety of different materials (see, e.g., U.S. Pat. Nos. 6,423,551; 6,251,303; 6,319,426; 6,426,513; 6,444,143; and 6,649,138; all of which are incorporated herein by reference). In some embodiments, QDs are solubilized using amphiphilic polymers, including, but not limited to, octylamine-modified low molecular weight polyacrylic acid, polyethylene-glycol (PEG)-derivatized phospholipids, polyanhydrides, block copolymers, etc. (Gao, 2004, *Nat. Biotechnol.*, 22:969; incorporated herein by reference).

In some embodiments, provided nanoparticle compositions comprise metal particles. In some embodiments, provided nanoparticle compositions comprise one or more metals selected from the group consisting of gold, silver, platinum, iron, cobalt, zinc, cadmium, nickel, gadolinium, chromium, copper, manganese, palladium, tin, alloys thereof, oxides thereof, and/or combinations thereof. In some embodiments, provided nanoparticle compositions comprise aggregates of metals. In some embodiments, provided nanoparticle compositions comprise core/shell particles (e.g., having a silver core with an outer shell of gold, or vice versa). In some embodiments, provided nanoparticle compositions comprise particles containing a metal core and a nonmetallic inorganic or organic outer shell. In some embodiments, provided nanoparticle compositions comprise particles containing a nonmetallic inorganic or organic core and a metal outer shell. In some embodiments, the nonmetallic core or shell comprises or consists of a dielectric material such as silica. In some embodiments, provided nanoparticle compositions comprise composite particles, e.g., in which a plurality of metal particles are embedded or trapped in a nonmetal (e.g., a polymer or a silica shell). In some embodiments, provided nanoparticle compositions comprise hollow metal particles (e.g., hollow nanoshells) having an interior space or cavity. In some embodiments, provided nanoparticle compositions comprise a nanoshell comprising two or more concentric hollow spheres.

In some embodiments, provided nanoparticle compositions can be prepared using any available method in the art. In some embodiments, provided nanoparticle compositions are prepared by nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. In some embodiments, provided nanoparticle compositions are prepared by aqueous and organic solvent syntheses (Pellegrino et al., 2005, *Small*, 1:48; Murray et al., 2000, *Ann. Rev. Mat. Sci.*, 30:545; and Trindade et al., 2001, *Chem. Mat.*, 13:3843; all of which are incorporated herein by reference). In some embodiments, provided nanoparticle compositions are prepared by nanoprecipitation or spray drying. Conditions used in preparing particles may be altered to yield particles of a desired size or property (e.g., hydrophobicity, hydrophilicity, external morphology, "stickiness," shape, etc.). In general, methods of preparing nanoparticles and/or conditions used (e.g., solvent, temperature, concentration, air flow rate, etc.) may depend on identity of functional elements (e.g., microbial mimic entities) associated with the particles and/or the composition of the polymer matrix.

Methods for making microparticles for delivery of encapsulated agents are described in the literature (see, e.g., Doubrow, Ed., "Microcapsules and Nanoparticles in Medicine and Pharmacy," CRC Press, Boca Raton, 1992; Mathiowitz et al., 1987, *J. Control. Release*, 5:13; Mathiowitz et al., 1987, *Reactive Polymers*, 6:275; and Mathiowitz et al., 1988, *J. Appl. Polymer Sci.*, 35:755; all of which are incorporated herein by reference).

Those of ordinary skill in the art will be familiar with appropriate strategies for preparing nanoparticle compositions. An extensive literature exists relating to different particular nanoparticles and/or types of nanoparticles. In some embodiments, nanoparticles are prepared as described in the Mellman Applications except that antigens are not included. In some embodiments, nanoparticles are prepared as described in the Emory Applications and/or references cited therein except that antigens are not included.

Microbial Mimic Entities

In some embodiments, provided nanoparticles comprise one or more microbial mimic entities, such that the provided nanoparticles mimic one or more characteristics or features of microbial (e.g., bacterial) cells. For example, in some embodiments, microbial mimic entities are or comprise entities known as pathogen-associated molecular patterns ("PAMPs"). In general, PAMPs are entities associated with bacterial cells that are recognized by cells of the innate immune system. In some embodiments, PAMPs are recognized by Toll-like receptors ("TLRs") and other pattern recognition receptors ("PRRs") in both plants and animals. In some embodiments, PAMPs are or comprise entities associated with the outer surface of a bacterial cell, including, but not limited to, membrane-associated proteins and/or peptides, receptors embedded in bacterial membranes, etc. Exemplary PAMPs include, but are not limited to, bacterial lipopolysaccharide ("LPS"), bacterial flagellin, lipoteichoic acid from gram positive bacteria, peptidoglycan, double-stranded RNAs ("dsRNAs"), unmethylated CpG motifs, any of the TLR ligands presented in Table 1, characteristic portions thereof, and/or combinations thereof.

TABLE 1

Exemplary TLRs and TLR Ligands

| TLR | TLR Ligand(s) |
|---|---|
| TLR1 | Multiple triacyl lipopeptides (e.g., from bacteria and mycobacteria), such as lipopeptide Pam3Cys-SK4 ("Pam") |
| TLR2 | Multiple glycolipids, lipopeptides and lipoproteins, such as lipopeptide Pam3Cys-SK4 ("Pam") |
|  | Lipoteichoic acid |
|  | Peptidoglycan |
|  | HSP70 |
|  | Zymosan |
|  | Heat shock proteins, such as Hsp60 |
| TLR3 | Double-stranded RNA |
|  | Single-stranded RNA |
|  | Poly(I:C) |
| TLR4 | lipopolysaccharide (LPS) |
|  | Monophosphoryl lipid A (MPL) |
|  | Several heat shock proteins |
|  | Fibrinogen |
|  | Heparin sulfate fragments |
|  | Hyaluronic acid fragments |
| TLR5 | Flagellin |
| TLR6 | Multiple diacyl lipopeptides |
|  | Lipoteichoic acid (LTA) |
|  | Zymosan |
| TLR7 | Imidazoquinolines (e.g., imiquimod and resiquimod) |
|  | Single-stranded RNA, such as GU-rich single-stranded RNA |
|  | Loxoribine (a guanosine analog) |
|  | Bropirime |

TABLE 1-continued

Exemplary TLRs and TLR Ligands

| TLR | TLR Ligand(s) |
|---|---|
| TLR8 | Imidazoquinolines (e.g., imiquimod and resiquimod) |
| | GU-rich single-stranded RNA |
| | Small synthetic compounds |
| | Single-stranded RNA |
| TLR9 | Unmethylated CpG DNA |
| | Hemazoin crystals |
| | Double-stranded DNA |
| TLR10 | |
| TRL11 | *Toxoplasma gondii* profilin |
| | Uropathogenic-bacteria-derived protein |

In some embodiments, microbial mimic entities are encapsulated within nanoparticles. In some embodiments, microbial mimic entities are at least partly associated with the surface of nanoparticles. In some embodiments, microbial mimic entities are completely-surface associated in that they are present on nanoparticle surfaces and not elsewhere in nanoparticle compositions (e.g., separate from and/or within nanoparticles).

In some embodiments, provided nanoparticle compositions contain certain functional elements (e.g., microbial mimic entities) in certain combinations and/or ratios. In some embodiments, provided nanoparticle compositions comprise a first functional element and a second functional element at a ratio of about 0.01:1, about 0.02:1, about 0.05:1, about 0.1:1, about 0.2:1, about 0.3:1, about 0.4:1, about 0.5:1, about 0.6:1, about 0.7:1, about 0.8:1, about 0.9:1, about 1:1, about 1:2, about 1:3, about 1:4, about 1:5, about 1:6, about 1:7, about 1:8, about 1:9, about 1:10, about 1:20, about 1:50, or about 1:100. In some embodiments, provided nanoparticle compositions contain LPS only. In some embodiments, provided nanoparticle compositions contain unmethylated CpG motifs only. In some embodiments, provided nanoparticle compositions contain both LPS and unmethylated CpG motifs. In some embodiments, provided nanoparticle compositions contain LPS and unmethylated CpG motifs at a ratio of about 0.01:1, about 0.02:1, about 0.05:1, about 0.1:1, about 0.2:1, about 0.3:1, about 0.4:1, about 0.5:1, about 0.6:1, about 0.7:1, about 0.8:1, about 0.9:1, about 1:1, about 1:2, about 1:3, about 1:4, about 1:5, about 1:6, about 1:7, about 1:8, about 1:9, about 1:10, about 1:20, about 1:50, or about 1:100.

In some embodiments, provided nanoparticle compositions comprise at least two PAMPs that are ligands for different TLRs. In some embodiments, provided nanoparticle compositions comprise one or more PAMPs selected from the group consisting of TLR4, 5, 7, and 8 ligands. In some embodiments, provided nanoparticle compositions comprise one or more PAMPs selected from the group consisting of TLR4 and 5 ligands. In some embodiments, provided nanoparticle compositions comprise one or more PAMPs selected from the group consisting of TLR2 and 4 ligands. In some embodiments, provided nanoparticle compositions comprise one or more PAMPs selected from the group consisting of TLR2 and 5 ligands. In some embodiments, provided nanoparticle compositions comprise one or more PAMPs selected from the group consisting of TLR2, 4, 5, and 11 ligands. In some embodiments, provided nanoparticle compositions comprise one or more PAMPs selected from the group consisting of TLR3, 7, 8, and 9 ligands. In some embodiments, provided nanoparticle compositions comprise one or more PAMPs selected from the group consisting of TLR3, 6, 7, and 9 ligands. In some embodiments, provided nanoparticle compositions comprise one or more PAMPs selected from the group consisting of TLR2, 3, 4, 5, and 9 ligands. In some embodiments, provided nanoparticle compositions comprise one or more PAMPs selected from the group consisting of TLR4, 5, 7, and 8 ligands. In some embodiments, provided nanoparticle compositions comprise one or more PAMPs selected from the group consisting of TLR1, 2, 3, and 6 ligands. In some embodiments, provided nanoparticle compositions comprise one or more PAMPs selected from the group consisting of TLR2, 5, and 8 ligands. In some embodiments, provided nanoparticle compositions comprise one or more PAMPs selected from the group consisting of TLR3, 4, 7, 8, and 9 ligands. In some embodiments, TLR ligands are present in specified ratios relative to one another.

In some embodiments, provided nanoparticle compositions comprise a population of provided nanoparticles, wherein the population is or comprises a mixture of more than one type of nanoparticle. In some embodiments, a population of provided nanoparticles at least two different types of provided nanoparticles, wherein the provided nanoparticles differ in the identity and/or amount of functional elements (e.g., microbial mimic entities) associated with the particles. To give but one example, one-third of a population of provided nanoparticles may contain provided nanoparticles containing LPS moieties, and two-thirds of the population may contain provided nanoparticles containing unmethylated CpG motifs.

Surface Moieties

In some embodiments, provided nanoparticles comprise one or more surface moieties that, for example, target relevant polymer particles to one or more particular tissues and/or impart to the relevant particles one or more attributes (e.g., immunological attributes) of a microbial cell (i.e., are microbial mimic entities).

In some embodiments, surface moieties are covalently associated with nanoparticle surfaces. In some embodiments, surface moieties are covalently bound directly to a nanoparticle surface. In some embodiments, surface moieties are covalently bound to a linker or other moiety (e.g., an adaptor moiety) that is covalently bound to a nanoparticle surface. In some embodiments, a surface moiety is covalently attached to a nanoparticle surface by way of an interaction selected from the group consisting of amide bonds, ester bonds, carbon-carbon bonds, disulfide bonds, "click" chemistry, and/or combinations thereof.

In some embodiments, surface moieties are non-covalently associated with a nanoparticle surface. In some embodiments, a surface moiety is non-covalently attached to a nanoparticle surface in that it is embedded within the nanoparticle surface (e.g., is intercalated within a polymeric matrix at the particle surface). In some embodiments, a surface moiety is non-covalently attached to a nanoparticle surface by way of an interaction selected from the group consisting of hydrophobic interactions, electrostatic interactions, polar interactions, affinity interactions, metal coordination, hydrogen bonding, II stacking interactions, van der Waals interactions, magnetic interactions, dipole-dipole interactions, and/or combinations thereof. For example, in some embodiments, a surface moiety is attached to a nanoparticle surface by way of an interaction between complementary affinity tags, one of which is attached (e.g., covalently bound to) the nanoparticle surface (whether directly or indirectly), and one of which is attached to the surface moiety. Exemplary affinity tag pairs include, but are not limited to, epitope/antibody, biotin/avidin, biotin/streptavidin, biotin/neutravidin, glutathione-S-transferase/glutathione, maltose binding protein/amylase, histidine/nickel-nitrolotriaceteic acid (Ni-NTA), maltose binding protein/maltose, and/or complementary single-stranded nucleic acids. Examples of suitable epitopes which may be used for epitope/antibody binding pairs include, but are not limited to, HA, FLAG, c-Myc, glutatione-S-transferase, $His_6$ (SEQ ID NO: 1), GFP, DIG, biotin and avidin. Antibodies (e.g., monoclonal antibodies, polyclonal antibodies, and/or antigen-binding fragments thereof) which bind to these epitopes are well known in the art.

In general, a moiety is considered to be a "surface moiety" if it is available for interaction with (e.g., detection by) an entity or agent that is contacted with a nanoparticle composition after the nanoparticle composition is produced and under conditions that preserve structural integrity of the nanoparticles, so that the contacted entity or agent is not exposed to contents of nanoparticles' interior.

In some embodiments, provided nanoparticle compositions comprise at least 1, at least 2, at least 3, at least 4, at least 5, at least 6, at least 7, at least 8, at least 9, or at least 10 surface moieties. In some embodiments, a single provided nanoparticle is associated with at least 1, at least 2, at least 3, at least 4, at least 5, at least 6, at least 7, at least 8, at least 9, at least 10, at least 20, at least 50, at least 100, or more identical surface moieties. In some embodiments, a single provided nanoparticle is associated with at least at least 1, at least 2, at least 3, at least 4, at least 5, at least 6, at least 7, at least 8, at least 9, or at least 10 different surface moieties. In some embodiments, provided nanoparticle compositions do not comprise any surface moieties.

In some embodiments, provided nanoparticle compositions contain certain surface moieties in certain combinations and/or ratios. In some embodiments, provided nanoparticle compositions contain a first surface moiety and a second surface moiety at a ratio of about 0.01:1, about 0.02:1, about 0.05:1, about 0.1:1, about 0.2:1, about 0.3:1, about 0.4:1, about 0.5:1, about 0.6:1, about 0.7:1, about 0.8:1, about 0.9:1, about 1:1, about 1:2, about 1:3, about 1:4, about 1:5, about 1:6, about 1:7, about 1:8, about 1:9, about 1:10, about 1:20, about 1:50, or about 1:100.

In some embodiments, provided nanoparticle compositions contain functional elements (e.g., microbial mimic entities) present at different locations within the context of a nanoparticle. In some embodiments, provided nanoparticle compositions contain a first set of functional elements (e.g., microbial mimic entities) present on a nanoparticle surface and a second set of functional elements (e.g., microbial mimic entities) encapsulated within the nanoparticle. In some embodiments, provided nanoparticle compositions contain a first set of functional elements (e.g., microbial mimic entities) present on a nanoparticle surface and a second set of functional elements (e.g., microbial mimic entities) encapsulated within the nanoparticle, wherein the first and second sets are present at a ratio of about 0.01:1, about 0.02:1, about 0.05:1, about 0.1:1, about 0.2:1, about 0.3:1, about 0.4:1, about 0.5:1, about 0.6:1, about 0.7:1, about 0.8:1, about 0.9:1, about 1:1, about 1:2, about 1:3, about 1:4, about 1:5, about 1:6, about 1:7, about 1:8, about 1:9, about 1:10, about 1:20, about 1:50, or about 1:100.

Uses

The present invention provides methods and compositions for the treatment and/or prevention of allergy. In some embodiments, provided nanoparticle compositions are useful as vaccines to prevent and/or delay the onset of an allergic reaction. In some embodiments, provided nanoparticle compositions are useful as vaccines to lessen the severity and/or duration of a future allergic reaction. In some embodiments, provided nanoparticle compositions are useful as therapeutics to alleviate and/or arrest an allergic reaction in progress.

In general, provided nanoparticle compositions may be used for treatment and/or prevention of any type of allergy. In some embodiments, provided nanoparticle compositions may be used for treatment and/or prevention of an allergy associated with one or more protein allergens presented in the Appendix. In some embodiments, provided nanoparticle compositions may be used for treatment and/or prevention of allergies associated with anaphylactic allergens, e.g., food allergens, insect allergens, and rubber allergens (e.g., from latex).

Food allergies are mediated through the interaction of IgE to specific proteins contained within the food. Examples of common food allergens include proteins from nuts (e.g., from peanut, walnut, almond, pecan, cashew, hazelnut, pistachio, pine nut, brazil nut), dairy products (e.g., from egg, milk), seeds (e.g., from sesame, poppy, mustard), soybean, wheat, and fish (e.g., shrimp, crab, lobster, clams, mussels, oysters, scallops, crayfish).

Examples of common insect allergens include, but are not limited to, proteins from insects such as fleas, ticks, ants, cockroaches, and bees.

Many allergens elicit a reaction when ingested, inhaled, and/or injected. Allergens can also elicit a reaction based solely on contact with the skin. Latex is a well known example. Latex products are manufactured from a milky fluid derived from the rubber tree (*Hevea brasiliensis*) and other processing chemicals. A number of the proteins in latex can cause a range of allergic reactions. Many products contain latex, such as medical supplies and personal protective equipment. Two types of reactions can occur in persons sensitive to latex: local allergic dermatitis and immediate systemic hypersensitivity (or anaphylaxis).

Local allergic dermatitis develops within a short time after exposure to latex and generally includes symptoms of urticaria or hives. The reaction is allergic and triggered by direct contact, not inhalation (Sussman et al., 1991, *JAMA*, 265:2844; incorporated herein by reference). Symptoms of immediate systemic hypersensitivity vary from skin and respiratory problems (e.g., urticaria, hives, rhinoconjunctivitis, swelling of lips, eyelids, and throat, wheezing, and coughing) to anaphylaxis which may progress to hypotension and shock. Such a reaction may be triggered by inhalation or skin exposure to the allergen.

In some embodiments, the present invention encompasses the recognition that provided nanoparticle compositions may be useful for treating and/or preventing a single allergy, even though no allergy-specific antigen is included. In some embodiments, the present invention encompasses the recognition that provided nanoparticle compositions may be useful for treating and/or preventing multiple different allergies. In some embodiments, the present invention encompasses the recognition that provided nanoparticle compositions may be useful for treating and/or preventing all of a subject's allergies. In some embodiments, the present invention encompasses the recognition that provided nanoparticle compositions may be useful for treating and/or preventing substantially all of a subject's allergies.

In some embodiments, the present invention encompasses the recognition that provided nanoparticle compositions may be useful for treating and/or preventing multiple different allergies in a single patient. For example, subjects suffering from and/or susceptible to allergy are frequently allergic to more than one allergen, e.g., at least 1, at least 2, at least 3, at least 4, at least 5, at least 6, at least 7, at least 8, at least 9, at least 10, at least 15, at least 20, at least 25, or more different allergens. Thus, in some embodiments, an provided nanoparticle composition may be used for treating and/or preventing at least 1, at least 2, at least 3, at least 4, at least 5, at least 6, at least 7, at least 8, at least 9, at least 10, at least 15, at least 20, at least 25, or more different allergies in a single patient. In some embodiments, an provided nanoparticle composition is administered to a subject suffering from and/or susceptible to multiple different allergies, e.g., at least 1, at least 2, at least 3, at least 4, at least 5, at least 6, at least 7, at least 8, at least 9, at least 10, at least 15, at least 20, at least 25, or more different allergies, such that the subject's symptoms are reduced and/or improved. In some embodiments, an provided nanoparticle composition is administered to a subject suffering from and/or susceptible to multiple different allergies, e.g., at least 1, at least 2, at least 3, at least 4, at least 5, at least 6, at least 7, at least 8, at least 9, at least 10, at least 15, at least 20, at least 25, or more different allergies, such that onset of the subject's symptoms is delayed.

In some embodiments, provided nanoparticle compositions effectively treat and/or prevent all of a subject's allergies. In some embodiments, provided nanoparticle compositions effectively treat and/or prevent substantially all of a subject's allergies. In some embodiments, provided nanoparticle compositions are useful as a "pan-allergy" treatment, meaning that provided nanoparticle compositions are useful for treatment and/or prevention of all of a subject's allergies. Without wishing to be bound by any one particular theory, provided nanoparticle compositions may function to suppress and/or decrease a subject's $T_H2$-type responses and/or enhance and/or increase a subject's $T_H1$-type responses.

In some embodiments, provided nanoparticle compositions effectively treat and/or prevent all of a subject's allergies falling into a particular class of allergy. In some embodiments, exemplary "classes" of allergies include, but are not limited to, anaphylactic allergies and non-anaphylactic allergies. In some embodiments, exemplary "classes" of allergies include, but are not limited to food allergies, insect allergies, pet dander allergies, pollen allergies, grass allergies, rubber allergies, and so forth. Thus, in some embodiments, provided nanoparticle compositions may be useful for treating all of a subject's food allergies. In some embodiments, exemplary "classes" of allergies include, but are not limited to, particular individual foods which contain multiple allergens. For example, there are at least eleven known peanut allergen proteins. Thus, in some embodiments, a "class" of allergies is "peanut" allergy, and provided nanoparticle compositions may be useful for treating all of a subject's allergies associated with all seven different peanut allergen proteins.

In some embodiments, the present invention involves administration of at least one provided nanoparticle composition according to a dosing regimen sufficient to achieve a reduction in the degree and/or prevalence of allergy of at least about 20%; in some embodiments according to a dosing regimen sufficient to achieve a reduction of at least about 25%; in some embodiments according to a dosing regimen sufficient to achieve a reduction of at least about 30%; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In some embodiments, the present invention involves administration of at least one provided nanoparticle composition according to a dosing regimen sufficient to achieve a reduction in the degree and/or prevalence of allergy of at least about 20% in a specified percentage of a population of patients to which the composition was administered; in some embodiments according to a dosing regimen sufficient to achieve a reduction of at least about 25% in a specified percentage of a population of patients to which the composition was administered; in some embodiments according to a dosing regimen sufficient to achieve a reduction of at least about 30% in a specified percentage of a population of patients to which the composition was administered; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more in a specified percentage of a population of patients to which the composition was administered. In some embodiments, the specified percentage of population of patients to which the composition was administered is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. To give but a few illustrative examples, in some embodiments, the present invention involves administration of at least one provided nanoparticle composition according to a dosing regimen sufficient to achieve a reduction in the degree and/or prevalence of allergy of at least about 20% in at least about 50% of the population of patients to which the composition was administered. In some embodiments, the present invention involves administration of at least one provided nanoparticle composition according to a dosing regimen sufficient to achieve a reduction in the degree and/or prevalence of allergy of at least about 30% in at least about 50% of the population of patients to which the composition was administered.

In some embodiments, the present invention involves administration of at least one provided nanoparticle composition according to a dosing regimen sufficient to achieve a delay in the onset of allergy.

In some embodiments, methods and/or uses encompassed by the present invention are not limited to treating allergy in humans, but may be used to treat allergy in any animal including but not limited to mammals, e.g., bovine, canine, feline, caprine, ovine, porcine, murine, and equine species, etc.

Compositions and Formulations

As noted herein, the present invention provides compositions comprising one or more provided nanoparticle compositions. Provided nanoparticle compositions may be formulated for an appropriate route of delivery.

In some embodiments, the present invention provides compositions (e.g., pharmaceutical compositions) comprising at least one provided nanoparticle composition. Such a composition may be formulated for any route of delivery, including, but not limited to, oral (PO), intravenous (IV), intramuscular (IM), intra-arterial (IA), intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, liniments, ointments, powders, gels, drops, etc.), mucosal, intranasal, buccal, enteral, vitreal, sublingual; by intratracheal instillation, bronchial instillation, and/or inhalation; as an oral spray, nasal spray, and/or aerosol, and/or through a portal vein catheter; and/or combinations thereof.

In some embodiments, provided nanoparticle compositions are formulated with one or more immune system adjuvants. Exemplary adjuvants include, but are not limited to, preparations (including heat-killed samples, extracts, partially purified isolates, or any other preparation of a microorganism or macroorganism component sufficient to display adjuvant activity) of microorganisms such as *Listeria monocytogenes, Escherichia coli* or others (e.g., bacille Calmette-Guerin (BCG), *Corynebacterium* species, *Mycobacterium* species, *Rhodococcus* species, *Eubacteria* species, *Bortadella* species, and *Nocardia* species); preparations of nucleic acids that include unmethylated CpG motifs (see, for example, U.S. Pat. No. 5,830,877; and published PCT applications WO96/02555, WO98/18810, WO98/16247, and WO98/40100; all of which are incorporated herein by reference); Avridine™ (N,N-dioctadecyl-N'N'-bis (2-hydroxyethyl)propanediamine) (M6 Pharmaceuticals, New York, N.Y.); niosomes (non-ionic surfactant vesicles) (Proteus Molecular Design, Macclesfield, UK); CRL 1005 (a synthetic ABA non-ionic block copolymer) (Vaxcel Corporation, Norcross, Ga.); and/or combinations thereof.

In some embodiments, an adjuvant is provided in the same formulation with the provided nanoparticle composition so that adjuvant and provided nanoparticle composition are delivered substantially simultaneously to the individual. In some embodiments, an adjuvant is provided in a separate formulation. Separate adjuvant may be administered prior to, simultaneously with, or subsequent to provided nanoparticle composition administration.

Formulations of provided nanoparticle compositions may be prepared by any appropriate method, for example as known or hereafter developed in the art of pharmacology. In general, such preparatory methods include the step of bringing a provided nanoparticle composition into association with one or more excipients, and then, if necessary and/or desirable, shaping and/or packaging the product into an appropriate form for administration, for example as or in a single- or multi-dose unit.

In some embodiments, compositions may be prepared, packaged, and/or sold in bulk, as a single unit dose, and/or as a plurality of single unit doses. As used herein, a "unit dose" is a discrete amount of the pharmaceutical composition comprising a predetermined amount of the provided nanoparticle composition. The amount of the provided nanoparticle composition is generally equal to the dosage of the provided nanoparticle which would be administered to a subject and/or a convenient fraction of such a dosage such as, for example, one-half or one-third of such a dosage.

Appropriate excipients for use in compositions (e.g., pharmaceutical compositions) may, for example, include one or more excipients such as solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. Alternatively or additionally, excipients such as cocoa butter and/or suppository waxes, coloring agents, coating agents, sweetening, flavoring, and/or perfuming agents can be utilized. Remington's *The Science and Practice of Pharmacy*, 21$^{st}$ Edition, A. R. Gennaro (Lippincott, Williams & Wilkins, Baltimore, Md., 2005; incorporated herein by reference) discloses various excipients used in formulating pharmaceutical compositions and known techniques for the preparation thereof.

In some embodiments, an appropriate excipient (e.g., a pharmaceutically and/or cosmetically acceptable excipient) is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

Liquid dosage forms for oral and/or parenteral administration include, but are not limited to, emulsions, microemulsions, solutions, suspensions, syrups, and/or elixirs. In addition to provided nanoparticle compositions, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of a provided nanoparticle composition, it may be desirable to slow the absorption of the provided nanoparticle composition from subcutaneous or intramuscular injection. This may be accomplished by the use of a liquid suspension of crystalline or amorphous material with poor water solubility. The rate of absorption of the provided nanoparticle composition then depends upon its rate of dissolution which, in turn, may depend upon crystal size and crystalline form. Alternatively, delayed absorption of a parenterally administered provided nanoparticle composition form is accomplished by dissolving or suspending the provided nanoparticle composition in an oil vehicle. Injectable depot forms are made by forming microencapsule matrices of the provided nanoparticle composition in biodegradable polymers such as polylactide-polyglycolide. Depending upon the ratio of provided nanoparticle composition to polymer and the nature of the particular polymer employed, the rate of provided nanoparticle composition release can be controlled. Examples of other biodegradable polymers include poly(orthoesters) and poly(anhydrides). Depot injectable formulations are prepared by entrapping the provided nanoparticle composition in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the provided nanoparticle composition.

Solid dosage forms for oral administration include capsules, tablets, pills, powders, and granules. In such solid dosage forms, the provided nanoparticle composition is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the provided nanoparticle composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In some embodiments, provided nanoparticle compositions are formulated for topical and/or transdermal delivery, e.g., as a cream, liniment, ointment, oil, foam, spray, lotion, liquid, powder, thickening lotion, or gel. Particular exemplary such formulations may be prepared, for example, as products such as skin softeners, nutritional lotion type emulsions, cleansing lotions, cleansing creams, skin milks, emollient lotions, massage creams, emollient creams, make-up bases, lipsticks, facial packs or facial gels, cleaner formulations such as shampoos, rinses, body cleansers, hair-tonics, or soaps, or dermatological compositions such as lotions, ointments, gels, creams, liniments, patches, deodorants, or sprays.

Those of ordinary skill in the art will appreciate that provided nanoparticle compositions may be incorporated into a device such as, for example, a patch. A variety of transdermal patch structures are known in the art; those of ordinary skill will appreciate that provided nanoparticle compositions may readily be incorporated into any of a variety of such structures. In some embodiments, a transdermal patch may further comprise a plurality of needles extending from one side of the patch that is applied to the skin, wherein needles extend from the patch to project through the stratum corneum of the skin. In some embodiments, needles do not rupture a blood vessel.

In some embodiments, a transdermal patch includes an adhesive. Some examples of adhesive patches are well known (for example, see U.S. Design Pat. 296,006; and U.S. Pat. Nos. 6,010,715; 5,591,767; 5,008,110; 5,683,712; 5,948,433; and 5,965,154; all of which are incorporated herein by reference). Adhesive patches are generally characterized as having an adhesive layer, which will be applied to a patient's skin, a depot or reservoir for holding a provided nanoparticle composition, and an exterior surface that prevents leakage of the provided nanoparticle composition from the depot. The exterior surface of a patch is typically non-adhesive.

In accordance with the present invention, a provided nanoparticle composition is incorporated into the patch so that it remains stable for extended periods of time. For example, a provided nanoparticle composition may be incorporated into a polymeric matrix that stabilizes the agent, and permits the agent to diffuse from the matrix and the patch. A provided nanoparticle composition may also be incorporated into the adhesive layer of the patch so that once the patch is applied to the skin, the provided nanoparticle composition may diffuse through the skin. In some embodiments, an adhesive layer may be heat-activated where temperatures of about 37° C. cause the adhesive to slowly liquefy so that the agent diffuses through the skin. The adhesive may remain tacky when stored at less than 37° C., and once applied to the skin, the adhesive loses its tackiness as it liquefies.

In some embodiments, an provided nanoparticle composition can be provided in a depot in the patch so that pressure applied to the patch causes the provided nanoparticle composition to be directed out of the patch (optionally through needles) and through the stratum corneum.

Suitable devices for use in administering provided nanoparticle compositions intradermally include short needle devices such as those described in U.S. Pat. Nos. 4,886,499; 5,190,521; 5,328,483; 5,527,288; 4,270,537; 5,015,235; 5,141,496; and 5,417,662; all of which are incorporated herein by reference. Intradermal compositions may be administered by devices which limit the effective penetration length of a needle into the skin, such as those described in PCT publication WO 99/34850 and functional equivalents thereof. Jet injection devices which deliver provided nanoparticle compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649, 912; 5,569,189; 5,704,911; 5,383,851; 5,893,397; 5,466, 220; 5,339,163; 5,312,335; 5,503,627; 5,064,413; 5,520, 639; 4,596,556; 4,790,824; 4,941,880; 4,940,460: and PCT Publications WO 97/37705 and WO 97/13537; all of which are incorporated herein by reference. Ballistic powder/particle delivery devices which use compressed gas to accelerate provided nanoparticle compositions in powder form through the outer layers of the skin to the dermis are suitable. Alternatively or additionally, conventional syringes may be used in the classical mantoux method of intradermal administration.

In some embodiments, compositions (e.g., pharmaceutical compositions) may be prepared, packaged, and/or sold in a formulation suitable for pulmonary administration via the buccal cavity. Such a formulation may comprise dry particles which comprise the provided nanoparticle composition and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the provided nanoparticle composition dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and the provided nanoparticle composition may constitute 0.1% to 20% (w/w) of the composition. The propellant may further comprise additional ingredients such as a liquid non-ionic and/or solid anionic surfactant and/or a solid diluent (which may have a particle size of the same order as particles comprising the provided nanoparticle composition).

In some embodiments, compositions (e.g., pharmaceutical compositions) formulated for pulmonary delivery may provide the provided nanoparticle composition in the form of droplets of a solution and/or suspension. Such formulations may be prepared, packaged, and/or sold as aqueous and/or dilute alcoholic solutions and/or suspensions, optionally sterile, comprising the provided nanoparticle composition, and may conveniently be administered using any nebulization and/or atomization device. Such formulations may further comprise one or more additional ingredients including, but not limited to, a flavoring agent such as saccharin sodium, a volatile oil, a buffering agent, a surface-active agent, and/or a preservative such as methylhydroxybenzoate. The droplets provided by this route of administration may have an average diameter in the range from about 0.1 nm to about 200 nm.

Formulations described herein as being useful for pulmonary delivery may be useful for intranasal delivery of a pharmaceutical composition. Another formulation suitable for intranasal administration is a coarse powder comprising the provided nanoparticle composition and having an average particle from about 0.2 μm to 500 μm. Such a formulation can be administered in the manner in which snuff is taken, i.e., by rapid inhalation through the nasal passage from a container of the powder held close to the nose.

Formulations suitable for nasal administration may, for example, comprise from about as little as 0.1% (w/w) and as much as 100% (w/w) of the provided nanoparticle composition, and may comprise one or more of the additional ingredients described herein. In some embodiments, pharmaceutical compositions may be prepared, packaged, and/or sold in a formulation suitable for buccal administration. Such formulations may, for example, be in the form of tablets and/or lozenges made using conventional methods, and may, for example, 0.1% to 20% (w/w) provided nanoparticle composition, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the provided nanoparticle composition. Such powdered, aerosolized, and/or aerosolized formulations, when dispersed, may have an average particle and/or droplet size in the range from about 0.1 nm to about 200 nm, and may further comprise one or more of the additional ingredients described herein.

In some embodiments, provided nanoparticle compositions may be prepared, packaged, and/or sold in a formulation suitable for ophthalmic administration. Such formulations may, for example, be in the form of eye drops including, for example, a 0.1/1.0% (w/w) solution and/or suspension of the provided nanoparticle composition in an aqueous or oily liquid excipient. Such drops may further comprise buffering agents, salts, and/or one or more other of the additional ingredients described herein. Other opthalmically-administrable formulations which are useful include those which comprise the provided nanoparticle composition in microcrystalline form and/or in a liposomal preparation. Ear drops and/or eye drops are contemplated as being within the scope of this invention.

Administration

As described herein, the present invention provides methods of administering provided nanoparticle compositions to a subject for treatment and/or prevention of allergy. In some embodiments, the present invention provides methods of treating and/or preventing allergy by administering provided nanoparticle compositions to a subject in need thereof.

In some embodiments, the present invention provides methods of administration of provided nanoparticle compositions via any route of delivery, including, but not limited to, oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, liniments, ointments, powders, gels, drops, etc.), mucosal, intranasal, buccal, enteral, vitreal, and/or sublingual administration; by intratracheal instillation, bronchial instillation, and/or inhalation; as an oral spray, nasal spray, and/or aerosol, and/or through a portal vein catheter; and/or combinations thereof. In some embodiments, the present invention provides methods of administration of provided nanoparticle compositions via oral administration. In some embodiments, the present invention provides methods of administration of provided nanoparticle compositions via sublingual administration (e.g., formulated as a toothpaste).

In some embodiments, provided nanoparticle compositions are administered to a subject in a single dose. In some embodiments, provided nanoparticle compositions are administered to a subject in multiple doses. In some embodiments, provided nanoparticle compositions are administered to a subject once every 20 years, once every 10 years, once every 5 years, once every 4 years, once every 3 years, once every 2 years, once per year, twice per year, 3 times per year, 4 times per year, 5 times per year, 6 times per year, 7 times per year, 8 times per year, 9 times per year, 10 times per year, 11 times per year, once per month, twice per month, three times per month, once per week, twice per week, three times per week, 4 times per week, 5 times per week, 6 times per week, daily, twice daily, 3 times daily, 4 times daily, 5 times daily, 6 times daily, 7 times daily, 8 times daily, 9 times daily, 10 times daily, 11 times daily, 12 times daily, or hourly. In some embodiments, provided nanoparticle compositions are administered to a subject via an initial dose with one or more booster doses. In some embodiments, one or more booster doses are administered 1 day, 2 days, 3 days, 4 days, 5 days, 6 days, 1 week, 2 weeks, 1 month, 2 months, 6 months, 1 year, 2 years, 5 years, 10 years, or longer than 10 years after the initial dose. In some embodiments, an initial dose comprises a series of doses administered over a period of time. For example, in some embodiments, an initial dose comprises a series of 1, 2, 3, 4, 5, 6, 7, 8, 9, 10, 11, 12, 13, 14, 15, 16, 17, 18, 19, 20, 21, 22, 23, 24, or more doses administered at regular intervals, e.g., intervals that are close in time to one another, such as 5 minute intervals, 10 minute intervals, 15 minute intervals, 20 minute intervals, 25 minute intervals, 30 minute intervals, 45 minute intervals, hourly intervals, every 2 hours, etc.

In some embodiments, an initial dose and booster doses contain the same amount of provided nanoparticle composition. In some embodiments, an initial dose and booster doses contain different amounts of provided nanoparticle composition. In certain embodiments, provided nanoparticle compositions at dosage levels sufficient to deliver from about 0.001 mg/kg to about 100 mg/kg, from about 0.01 mg/kg to about 50 mg/kg, preferably from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day. In some embodiments, provided nanoparticle compositions are formulated into a unit dose. In some embodiments, a unit dosage is about 10 mg, about 25 mg, about 50 mg, about 100 mg, about 250 mg, about 500 mg, about 1 g, about 5 g, about 10 g, about 25 g, about 50 g, about 100 g, or more than about 100 g. In some embodiments, the amount of provided nanoparticle composition present in a particular unit dose depends on the subject to which the composition is to be administered. To give but a few examples, in some embodiments, a unit dose appropriate for a mouse is smaller than a unit dose that is appropriate for a rat, which is smaller than a unit dose that is appropriate for a dog, is smaller than a unit dose that is appropriate for a human.

In some embodiments, provided nanoparticle compositions are administered to a subject in multiple doses over the course of the subject's entire lifespan. In some embodiments, provided nanoparticle compositions are administered to a subject in multiple doses over the course of several years (e.g., 2, 3, 4, 5, 6, 7, 8, 9, 10, 15, 20, 25, 30, 35, 40, 45, 50, 60, 70, 80, 90, or 100 years). In some embodiments, provided nanoparticle compositions are administered to a subject in multiple doses over the course of 1, 2, 3, 4, 5, 6, 7, 8, 9, 10, 11, or 12 months. In some embodiments, multiple doses are administered at regular intervals.

In some embodiments, prior to the first dose, a subject's baseline allergic response is determined by one or more of a variety of methods, including, but not limited to, (1) performing a prick skin test (PST) of one or more of the subject's 1, 2, 3, 4, 5, 6, 7, 8, 9, 10, 11, 12, 13, 14, 15, 16, 17, 18, 19, 20, or more than 20 allergens, and measuring the wheal and flare response to the PST; (2) measuring blood serum IgE levels; (3) noting the subject's own description of her typical symptoms (e.g., nature, severity, and/or duration of symptoms) upon exposure to one or more of her 1, 2, 3, 4, 5, 6, 7, 8, 9, 10, 11, 12, 13, 14, 15, 16, 17, 18, 19, 20, or more than 20 allergens; (4) exposing the subject to a certain dose of one or more of her 1, 2, 3, 4, 5, 6, 7, 8, 9, 10, 11, 12, 13, 14, 15, 16, 17, 18, 19, 20, or more than 20 allergens (e.g., if only a small or nonexistent risk of anaphylaxis); (5) measuring expression (e.g., levels, spatial distribution, temporal distribution, etc.), of one or more molecular markers, including, but not limited to, T-cell markers CD4+ and/or CD8+; (6) performing a basophil histamine release assay; and/or combinations thereof. In some embodiments, a subject's allergic response is monitored using any combination of methods, e.g. methods (1)-(6) described above, throughout the course of the treatment regimen and/or after the treatment regimen is completed, e.g., at regular intervals. In some embodiments, allergic response is monitored daily, weekly, bi-weekly, monthly, 6 times per year, 4 times per year, 3 times per year, 2 times per year, once per year, every 2 years, every 5 years, and/or every 10 years, etc.

In some embodiments, a subject is challenged with a single allergen and/or multiple allergens, e.g., a subset of the subject's allergens (e.g., allergens to which the subject is known to be allergic) and/or all of the subject's allergens (e.g., allergens to which the subject is known to be allergic). In some embodiments, allergy challenge is performed after 1 week, 2 weeks, 1 month, 2 months, 6 months, and 1 year after initiation of treatment.

Combination Therapy

In some embodiments, provided nanoparticle compositions are administered to a subject in combination with one or more other therapeutic agents, for example useful in the treatment of allergy, so the subject is simultaneously exposed to both the provided nanoparticle composition and the other therapeutic agent.

In some embodiments, a provided nanoparticle composition is found in a pharmaceutical formulation that is separate from and distinct from the pharmaceutical formulation containing the other therapeutic agent. In some embodiments, a provided nanoparticle composition is admixed with the composition comprising the other therapeutic agent. In other words, a provided nanoparticle composition is produced individually, and the provided nanoparticle composition is simply mixed with another composition comprising another therapeutic agent.

The particular combination of therapies (substances and/or procedures) to employ in a combination regimen will take into account compatibility of the desired substances and/or procedures and the desired therapeutic effect to be achieved. In some embodiments, provided nanoparticle compositions can be administered concurrently with, prior to, or subsequent to, one or more other therapeutic agents (e.g., desired known allergy therapeutics).

It will be appreciated that the therapies employed may achieve a desired effect for the same disorder (for example, an provided nanoparticle composition useful for treating allergy may be administered concurrently with a known allergy therapeutic that is also useful for treating allergy), or they may achieve different effects (for example, an provided nanoparticle composition that is useful for treating allergy may be administered concurrently with a therapeutic agent that is useful for alleviating adverse side effects, for instance, inflammation, nausea, etc.). In some embodiments, provided nanoparticle compositions in accordance with the invention are administered with a second therapeutic agent that is approved by the U.S. Food and Drug Administration (FDA).

By "in combination with" or "in conjunction with," it is not intended to imply that the substances and/or procedures must be administered at the same time and/or formulated for administration together, although these methods of administration are within the scope of the invention. Provided nanoparticle compositions can be administered concurrently with, prior to, or subsequent to, one or more other desired known allergy therapeutics. In general, each substance will be administered at a dose and/or on a time schedule determined for that agent.

In some embodiments, provided nanoparticle compositions include or are administered in combination with one or more other therapeutic agents. In some embodiments, exemplary known allergy therapeutics that can be administered in combination with provided nanoparticle compositions in accordance with the invention include, but are not limited to, any of the therapeutics described in U.S. Pat. Nos. 5,558,869, 5,973,121, 6,835,824, 6,486,311, and/or 7,485,708, and/or in US Patent Publication Numbers 2003/0035810, 2003/0202980, 2004/0208894, 2004/0234548, 2007/0213507, 2010/0166802, and/or 2011/0027298, all of which are incorporated herein by reference; antihistamines, glucocorticoids; epinephrine (adrenaline); theophylline; cromolyn sodium; anti-leukotrienes; Montelukast)(SINGULAIR®; Zafirlukast (ACCOLATE®); anti-cholinergics; decongestants; mast cell stabilizers; immunotherapy (progressively larger doses of a specific allergen); monoclonal anti-IgE antibodies (e.g., omalizumab); and/or combinations thereof.

Kits

The present invention provides kits comprising vaccine and/or therapeutic compositions including provided nanoparticles. In some embodiments, a kit may comprise (i) at least one provided nanoparticle composition; and (ii) at least one pharmaceutically acceptable excipient; and, optionally, (iii) instructions for use. In some embodiments, kits include multiple (e.g., 1, 2, 3, 4, 5, 6, 7, 8, 9, 10, 11, 12, 13, 14, 15, 16, 17, 18, 19, 20, or more) doses of provided nanoparticle compositions. In some embodiments, kits include multiple (e.g., 1, 2, 3, 4, 5, 6, 7, 8, 9, 10, 11, 12, 13, 14, 15, 16, 17, 18, 19, 20, or more) populations of provided nanoparticles having different functional elements (e.g., microbial mimic entities). In some embodiments, multiple populations of provided nanoparticles are packaged separately from one another in provided kits. In some embodiments, kits include provided nanoparticle compositions and one or more therapeutics selected from the group consisting of any of the therapeutics described in U.S. Pat. Nos. 5,558,869, 5,973,121, 6,835,824, 6,486,311, and/or 7,485,708, and/or in US Patent Publication Numbers 2003/0035810, 2003/0202980, 2004/0208894, 2004/0234548, 2007/0213507, 2010/0166802, and/or 2011/0027298, all of which are incorporated herein by reference; antihistamines, glucocorticoids; epinephrine (adrenaline); theophylline; cromolyn sodium; anti-leukotrienes; Montelukast) (SINGULAIR®); Zafirlukast (ACCOLATE®); anti-cholinergics; decongestants; mast cell stabilizers; immunotherapy (progressively larger doses of a specific allergen); monoclonal anti-IgE antibodies (e.g., omalizumab); and/or combinations thereof.

In some embodiments, the present invention provides pharmaceutical packs or kits including provided nanoparticle compositions to be used in treatment methods according to the present invention. In some embodiments, pharmaceutical packs or kits include preparations or pharmaceutical compositions containing provided nanoparticle compositions in one or more containers filled with optionally one or more additional ingredients of pharmaceutical compositions in accordance with the invention. In some embodiments, the pharmaceutical pack or kit includes an additional approved therapeutic agent (e.g., known allergy therapeutic) for use in combination therapies, as described herein. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include provided nanoparticle compositions and instructions for use. Pharmaceutical doses or instructions therefor may be provided in a kit for administration to an individual suffering from and/or susceptible to allergy.

EXEMPLIFICATION

Example 1

Pan-Allergy Vaccine Comprising Polymeric Nanoparticles

In this example, a provided nanoparticle composition is used to vaccinate a subject who is allergic to 1, 2, 3, 4, 5, 6, 7, 8, 9, 10, 11, 12, 13, 14, 15, 16, 17, 18, 19, 20, or more than 20 different allergens (including food allergens, insect allergens, pollen allergens, and/or combinations thereof). The provided nanoparticle composition comprises a population of polymeric nanoparticles (e.g., comprising PLA, PGA, PLGA, and/or combinations thereof) having the following characteristics:

10% nanoparticles with flagellin associated with the particle surface

90% nanoparticles with both CpG moieties encapsulated within the particles and LPS associated with the particle surface at a 1:1 ratio The provided nanoparticle composition is formulated for oral delivery (e.g., as a capsule, optionally with an enteric coating). The formulation contains about 10 mg, about 25 mg, about 50 mg, about 100 mg, about 250 mg, about 500 mg, about 1 g, about 5 g, about 10 g, about 25 g, about 50 g, about 100 g, or more than about 100 g of the provided nanoparticle composition.

Prior to the first dose, a subject's baseline allergic response is determined by one or more of a variety of methods, including, but not limited to, (1) performing a prick skin test (PST) of one or more of the subject's 1, 2, 3, 4, 5, 6, 7, 8, 9, 10, 11, 12, 13, 14, 15, 16, 17, 18, 19, 20, or more than 20 allergens, and measuring the wheal and flare response to the PST; (2) measuring blood serum IgE levels; (3) noting the subject's own description of her typical symptoms (e.g., nature, severity, and/or duration of symptoms) upon exposure to one or more of her 1, 2, 3, 4, 5, 6, 7, 8, 9, 10, 11, 12, 13, 14, 15, 16, 17, 18, 19, 20, or more than 20 allergens; (4) exposing the subject to a certain dose of one or more of her 1, 2, 3, 4, 5, 6, 7, 8, 9, 10, 11, 12, 13, 14, 15, 16, 17, 18, 19, 20, or more than 20 allergens (e.g., if only a small or nonexistent risk of anaphylaxis); (5) measuring expression (e.g., levels, spatial distribution, temporal distribution, etc.), of one or more molecular markers, including, but not limited to, T-cell markers CD4+ and/or CD8+; (6) performing a basophil histamine release assay; and/or combinations thereof. The subject's allergic response is monitored using any combination of methods, e.g. methods (1)-(6) described above, at regular intervals during the course of the treatment regimen and/or after the treatment regimen is completed. In some embodiments, allergic response is monitored daily, weekly, bi-weekly, monthly, 6 times per year, 4 times per year, 3 times per year, 2 times per year, once per year, every 2 years, every 5 years, and/or every 10 years, etc.

The provided nanoparticle composition is orally administered five times separated by 30 minutes (intra-subject dose escalation) on Day 1 to assess the safety of the proposed range of doses, and/or identify the maximum tolerated dose (MTD). The MTD or highest proposed dose, whichever is lower, is then administered once daily (qd) starting on Day 2 for 14 days, for 1 month, for 2 months, for 6 months, and/or for 1 year.

The subject is challenged with either (1) a single one of her 1, 2, 3, 4, 5, 6, 7, 8, 9, 10, 11, 12, 13, 14, 15, 16, 17, 18, 19, 20, or more than 20 allergens, (2) a subset of her 1, 2, 3, 4, 5, 6, 7, 8, 9, 10, 11, 12, 13, 14, 15, 16, 17, 18, 19, 20, or more than 20 allergens, or (3) all 1, 2, 3, 4, 5, 6, 7, 8, 9, 10, 11, 12, 13, 14, 15, 16, 17, 18, 19, 20, or more than 20 of her allergens after 1 week, 2 weeks, 1 month, 2 months, 6 months, and 1 year after initiation of treatment. The severity and duration of the subject's allergic reaction to all 1, 2, 3, 4, 5, 6, 7, 8, 9, 10, 11, 12, 13, 14, 15, 16, 17, 18, 19, 20, or more than 20 of her allergens is increasingly improved over the duration of her treatment.

Example 2

Pan-Allergy Vaccine Comprising Solid Nanoparticles

In this example, a provided nanoparticle composition is used to vaccinate a subject who is allergic to 1, 2, 3, 4, 5, 6, 7, 8, 9, 10, 11, 12, 13, 14, 15, 16, 17, 18, 19, 20, or more than 20 different allergens (including food allergens, insect allergens, pollen allergens, and/or combinations thereof). The provided nanoparticle composition comprises a population of solid nanoparticles (e.g., one or more of quantum dots, metal particles, ceramic particles, and/or combinations thereof) having the following characteristics:
- 10% nanoparticles with flagellin associated with the particle surface
- 90% nanoparticles with both CpG moieties encapsulated within the particles and LPS associated with the particle surface at a 1:1 ratio The provided nanoparticle composition is formulated for oral delivery (e.g., as a capsule, optionally with an enteric coating). The formulation contains about 10 mg, about 25 mg, about 50 mg, about 100 mg, about 250 mg, about 500 mg, about 1 g, about 5 g, about 10 g, about 25 g, about 50 g, about 100 g, or more than about 100 g of the provided nanoparticle composition.

Prior to the first dose, a subject's baseline allergic response is determined by one or more of a variety of methods, including, but not limited to, (1) performing a prick skin test (PST) of one or more of the subject's 1, 2, 3, 4, 5, 6, 7, 8, 9, 10, 11, 12, 13, 14, 15, 16, 17, 18, 19, 20, or more than 20 allergens, and measuring the wheal and flare response to the PST; (2) measuring blood serum IgE levels; (3) noting the subject's own description of her typical symptoms (e.g., nature, severity, and/or duration of symptoms) upon exposure to one or more of her 1, 2, 3, 4, 5, 6, 7, 8, 9, 10, 11, 12, 13, 14, 15, 16, 17, 18, 19, 20, or more than 20 allergens; (4) exposing the subject to a certain dose of one or more of her 1, 2, 3, 4, 5, 6, 7, 8, 9, 10, 11, 12, 13, 14, 15, 16, 17, 18, 19, 20, or more than 20 allergens (e.g., if only a small or nonexistent risk of anaphylaxis); (5) measuring expression (e.g., levels, spatial distribution, temporal distribution, etc.), of one or more molecular markers, including, but not limited to, T-cell markers CD4+ and/or CD8+; (6) performing a basophil histamine release assay; and/or combinations thereof. The subject's allergic response is monitored using any combination of methods, e.g. methods (1)-(6) described above, at regular intervals during the course of the treatment regimen and/or after the treatment regimen is completed. In some embodiments, allergic response is monitored daily, weekly, bi-weekly, monthly, 6 times per year, 4 times per year, 3 times per year, 2 times per year, once per year, every 2 years, every 5 years, and/or every 10 years, etc.

The provided nanoparticle composition is orally administered five times separated by 30 minutes (intra-subject dose escalation) on Day 1 to assess the safety of the proposed range of doses, and/or identify the maximum tolerated dose (MTD). The MTD or highest proposed dose, whichever is lower, is then administered once daily (qd) starting on Day 2 for 14 days, for 1 month, for 2 months, for 6 months, and/or for 1 year.

The subject is challenged with either (1) a single one of her 1, 2, 3, 4, 5, 6, 7, 8, 9, 10, 11, 12, 13, 14, 15, 16, 17, 18, 19, 20, or more than 20 allergens, (2) a subset of her 1, 2, 3, 4, 5, 6, 7, 8, 9, 10, 11, 12, 13, 14, 15, 16, 17, 18, 19, 20, or more than 20 allergens, or (3) all 1, 2, 3, 4, 5, 6, 7, 8, 9, 10, 11, 12, 13, 14, 15, 16, 17, 18, 19, 20, or more than 20 of her allergens after 1 week, 2 weeks, 1 month, 2 months, 6 months, and 1 year after initiation of treatment. The severity and duration of the subject's allergic reaction to all 1, 2, 3, 4, 5, 6, 7, 8, 9, 10, 11, 12, 13, 14, 15, 16, 17, 18, 19, 20, or more than 20 of her allergens is increasingly improved over the duration of her treatment.

Example 3

Pan-Allergy Vaccine Comprising Nanoparticles Described in Mellman Applications

The present Example describes preparation of nanoparticle compositions substantially based on the Mellman Applications but incorporating the inventive insight described herein that useful allergy vaccine compositions, and particularly useful multiple-allergy or pan-allergy vaccine compositions, can be prepared without including allergy-specific antigens. The Mellman Applications always include antigen in their described compositions, and indeed describe antigens as "needed in the design of effective vaccines" (paragraph 5 of US patent publication 2010/0104503, incorporated herein by reference; emphasis added). Moreover, the entire disclosures of the Mellman Applications is drawn to "stimulating immune responses to a specific pathogen" (paragraph 21 US patent publication 2010/0104503, incorporated herein by reference; emphasis added), and they include extensive discussion of antigen delivery and uptake of delivered antigens by antigen-presenting cells. Indeed, their definition of "immune response" is development of a cellular and/or humoral response "directed against an antigen" (paragraph 37 of US patent publication 2010/0104503, incorporated herein by reference; emphasis added). The present invention, however, provides the insight that such antigens are not required for beneficial effect and, in fact, that removal of antigens can provide compositions with multiple-allergy or pan-allergy therapeutic and/or prophylactic utility.

As described in the Mellman Applications, nanoparticle compositions can desirably be prepared from one or more polymeric nanoparticles, adaptor elements, functional elements, adjuvants, contrast agents and/or other markers, and/or combinations thereof, as described in further detail in the sections below, except that nanoparticle compositions in accordance with the present invention do not contain any allergy-specific antigens.

Polymeric Nanoparticles

As used herein, nanoparticles generally refers to particles in the range of between 500 nm to less than 0.5 nm, preferably having a diameter that is between 50 and 500 nm.

The polymer that forms the core of the modular vaccine nanoparticle may be any biodegradable or non-biodegradable synthetic or natural polymer. In some embodiments, the polymer is a biodegradable polymer. These systems have several features that make them ideal materials for the fabrication of a vaccine nanodevice: 1) control over the size range of fabrication, down to 100 nm or less, an important feature for passing through biological barriers; 2) reproducible biodegradability without the addition of enzymes or cofactors; 3) well-understood fabrication methodologies that offer flexibility over the range of parameters that can be used for fabrication, including choices of the polymer material, solvent, stabilizer, and scale of production; and 4) control over surface properties facilitating the introduction of modular functionalities into the surface.

In some embodiments, biodegradable polymers include synthetic polymers that degrade by hydrolysis such as poly(hydroxy acids), such as polymers and copolymers of lactic acid and glycolic acid, polyanhydrides, poly(ortho)esters, polyesters, polyurethanes, poly(butic acid), poly(valeric acid), poly(caprolactone), poly(hydroxyalkanoates), and poly(lactide-co-caprolactone).

In some embodiments, natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, non-biodegradable polymers can be used, especially hydrophobic polymers. In some embodiments, non-biodegradable polymers include ethylene vinyl acetate, poly(meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

In some embodiments, other suitable biodegradable and non-biodegradable polymers include, but are not limited to, polyanhydrides, polyamides, polycarbonates, polyalkylenes, polyalkylene oxides such as polyethylene glycol, polyalkylene terepthalates such as poly(ethylene terephthalate), polyvinyl alcohols, polyvinyl ethers, polyvinyl esters, polyethylene, polypropylene, poly(vinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate).

In some embodiments, polymers may be used alone, as physical mixtures (blends), or as co-polymers. In some embodiments, nanoparticle compositions comprise polymers fabricated from polylactides (PLA) and copolymers of lactide and glycolide (PLGA).

In some embodiments, polymers may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

In some embodiments, rate controlling polymers are included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). In some embodiments, gastrosoluble polymers, such as EUDRAGIT® E100 or enteric polymers such as EUDRAGIT® L100-55D, L100 and S100 are blended with rate controlling polymers to achieve pH dependent release kinetics. In some embodiments, hydrophilic polymers such as alginate, polyethylene oxide, carboxymethylcellulose, and hydroxyethylcellulose are used as rate controlling polymers.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

Adaptor Elements

In general, adaptor elements associate with nanoparticles and provide substrates that facilitate the modular assembly and disassembly of functional elements to nanoparticles. Adaptor elements may associate with nanoparticles through a variety of interactions including, but not limited to, hydrophobic interactions, electrostatic interactions, and/or covalent coupling.

In some embodiments, adaptor elements associate with polymeric nanoparticles noncovalently through hydrophobic interactions. Examples of adaptor elements which may associate with nanoparticles via hydrophobic interactions include, but are not limited to, fatty acids, hydrophobic or amphipathic peptides or proteins, and polymers. These classes of adaptor elements may also be used in any combination or ratio. In some embodiments, the association of adaptor elements with nanoparticles facilitates a prolonged presentation of functional elements which can last for several weeks.

In some embodiments, adaptor elements are attached to polymeric nanoparticles through covalent interactions through various functional groups. Functionality refers to conjugation of a molecule to the surface of the particle via a functional chemical group (carboxylic acids, aldehydes, amines, sulfhydryls and hydroxyls) present on the surface of the particle and present on the molecule to be attached.

In some embodiments, functionality is introduced during preparation of nanoparticles, for example during the emulsion preparation of nanoparticles by incorporation of stabilizers with functional chemical groups. Suitable stabilizers include hydrophobic or amphipathic molecules that associate with the outer surface of the nanoparticles.

In some embodiments, functionality is introduced after particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. In some embodiments, this second class includes a process whereby amphiphilic molecules such as fatty acids, lipids or functional stabilizers may be passively adsorbed and adhered to the particle surface, thereby introducing functional end groups for tethering to ligands.

In some embodiments, functionalization is carried out by "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a molecule such as a protein. The reaction is an N-nucleophilic substitution and results in a stable N-alkylcarbamate linkage of the molecule to the polymer. In some embodiments, "coupling" of the molecule to the "activated" polymer matrix occurs in the pH range of 9-10 and may take at least 24 hrs. The resulting molecule-polymer complex is stable and resists hydrolysis for extended periods of time.

In some embodiments, functionalization is carried out by use of 1-ethyl-3-(3-dimethylaminopropyl)carbodiimide (EDAC) or "water-soluble CDI" in conjunction with N-hydroxylsulfosuccinimide (sulfo NHS) to couple the exposed carboxylic groups of polymers to the free amino groups of molecules in a totally aqueous environment at the physiological pH of 7.0. Briefly, EDAC and sulfo-NHS form an activated ester with the carboxylic acid groups of the polymer which react with the amine end of a molecule to form a peptide bond. In some embodiments, the resulting peptide bond is resistant to hydrolysis. Use of sulfo-NHS in the reaction increases the efficiency of the EDAC coupling by a factor of ten-fold and provides for exceptionally gentle conditions that ensure the viability of the molecule-polymer complex.

By using either of these protocols it is possible to "activate" almost all polymers containing either hydroxyl or carboxyl groups in a suitable solvent system that will not dissolve the polymer matrix.

In some embodiments, a procedure for attaching molecules with free hydroxyl and carboxyl groups to polymers involves the use of the cross-linking agent, divinylsulfone. In some embodiments, this method is useful for attaching sugars or other hydroxylic compounds with bioadhesive properties to hydroxylic matrices. Briefly, activation involves the reaction of divinylsulfone to hydroxyl groups of the polymer, forming the vinylsulfonyl ethyl ether of the polymer. In some embodiments, vinyl groups couple to alcohols, phenols, and/or amines. In some embodiments, activation and coupling take place at pH 11. In some embodiments, the linkage is stable in the pH range from 1-8 and is suitable for transit through the intestine.

In some embodiments, any suitable coupling method known to those skilled in the art for the coupling of molecules and polymers with double bonds, including the use of UV crosslinking, may be used for attachment of molecules to the polymer.

In some embodiments, adaptor elements can be conjugated to affinity tags. In general, affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, $His_6$ (SEQ ID NO: 1), GFP, DIG, biotin and avidin. Antibodies (both monoclonal and polyclonal and antigen-binding fragments thereof) which bind to these epitopes are well known in the art.

In some embodiments, affinity tags that are conjugated to adaptor elements allow for highly flexible, modular assembly and disassembly of functional elements which are conjugated to affinity tags which form highly specific, noncovalent, physiochemical interactions with complementary affinity tags which are conjugated to adaptor elements. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the nanoparticles and their ratios.

In some embodiments, adaptor elements are coupled directly to functional elements in the absence of affinity tags, such as through direct covalent interactions. Adaptor elements can be covalently coupled to at least one species of functional element. Adaptor elements can be covalently coupled to a single species of functional element or with any combination of species of functional elements in any ratio.

In some embodiments, adaptor elements are conjugated to at least one affinity tag that provides for assembly and disassembly of modular functional elements which are conjugated to complementary affinity tags. In some embodiments, adaptor elements are fatty acids that are conjugated with at least one affinity tag. In some embodiments, adaptor elements are fatty acids conjugated with avidin or streptavidin. Such avidin/streptavidin-conjugated fatty acids allow for the attachment of a wide variety of biotin-conjugated functional elements.

In some embodiments, adaptor elements are provided on, or in the surface of, nanoparticles at a high density. This high density of adaptor elements allows for coupling of the nanoparticle to a variety of species of functional elements while still allowing for the functional elements to be present in high enough numbers to be efficacious.

Fatty Acids

In some embodiments, adaptor elements may include fatty acids. Fatty acids may be of any acyl chain length and may be saturated or unsaturated. In some embodiments, a fatty acid is palmitic acid. In some embodiments, suitable fatty acids include, but are not limited to, saturated fatty acids such as butyric, caproic, caprylic, capric, lauric, myristic, stearic, arachidic and behenic acid. In some embodiments, suitable fatty acids include, but are not limited to, unsaturated fatty acids such as oleic, linoleic, alpha-linolenic, arachidonic, eicosapentaenoic, docosahexaenoic, and erucic acid.

Hydrophobic or Amphipathic Peptides

In some embodiments, adaptor elements may include hydrophobic or amphipathic peptides. In some embodiments, peptides are sufficiently hydrophobic to preferentially associate with the polymeric nanoparticle over the aqueous environment. Amphipathic polypeptides useful as adaptor elements may be mostly hydrophobic on one end and mostly hydrophilic on the other end. Such amphipathic peptides may associate with polymeric nanoparticles through the hydrophobic end of the peptide and be conjugated on the hydrophilic end to a functional group.

Hydrophobic Polymers

In some embodiments, adaptor elements include hydrophobic polymers. Examples of hydrophobic polymers include, but are not limited to, polyanhydrides, poly(ortho) esters, and polyesters such as polycaprolactone.

Functional Elements

Functional elements which associate with the nanoparticles provide a number of different functions to the composition. In some embodiments, these functions include protection of the nanoparticle vaccine from hostile environments during transit in the gastrointestinal tract, transport through epithelial barriers, and/or targeting antigen presenting cells with high avidity. In some embodiments, functional elements may include dendritic cell recognition elements, epithelial cell recognition elements, pH-sensitive molecules which protect the composition from hydrolysis and degradation in low-pH environments, non-pH-sensitive molecules which protect the composition from hydrolysis and degradation in low-pH environments, and/or endosome-disrupting agents.

In some embodiments, nanoparticles may be associated with a single species of functional element or may be associated with any combination of disclosed functional elements in any ratio. In some embodiments, functional elements are directly associated with nanoparticles in the absence of adaptor elements. Functional elements may be directly associated with nanoparticles through covalent or noncovalent interactions, including, but not limited to, hydrophobic interactions and electrostatic interactions. Covalent attachment of functional elements can be achieved by introducing functionality to the polymeric nanoparticles using methods described above with respect to adaptor elements.

In some embodiments, functional elements are associated with nanoparticles through adaptor elements which directly associate with the nanoparticles. Functional elements may be directly, covalently coupled to adaptor elements or may couple to adaptor elements through complementary affinity tags conjugated to the adaptor and functional elements. Multiple different species of functional elements may be associated with nanoparticles in any desired ratio, for instance, by conjugating each species of functional element to a separate species of affinity tag. These functional elements may then associate with nanoparticles coated with adaptor elements conjugated to an appropriate ratio of complementary affinity tags. Multiple species of functional elements may also be associated with nanoparticles by covalently coupling each species of functional element at a desired ratio to adaptor elements.

In some embodiments, functional elements are conjugated to biotin. Biotin conjugation allows the functional elements to interact with adaptor elements conjugated with avidin, neutravidin or streptavidin.

Targeting Molecules for Professional Antigen Presenting Cells

Of the main types of antigen-presenting cells (B cell, macrophages and DCs), the DC is the most potent and is responsible for initiating all antigen-specific immune responses. One biological feature of DCs is their ability to sense conditions under which antigen is encountered, initiating a process of "DC maturation". Using receptors for various microbial and inflammatory products, DCs respond to antigen exposure in different ways depending on the nature of the pathogen (virus, bacteria, protozoan) encountered. This information is transmitted to T cells by altered patterns of cytokine release at the time of antigen presentation in lymph nodes, altering the type of T cell response elicited.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger, et al., J. Exp. Med., 194(6):769-79 (2001); Bonifaz, et al., J. Exp. Med., 196(12):1627-38 (2002); Bonifaz, et al., J. Exp. Med., 199(6):815-24 (2004)). In these experiments, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors.

Other receptors which may be targeted include the toll-like receptors (TLRs). TLRs recognize and bind to pathogen-associated molecular patterns (PAMPs). PAMPs target the TLR on the surface of the dendritic cell and signals internally. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

Targeting Molecules for Epithelial Cells

The potential efficacy of nanoparticle vaccine systems is determined in part by their route of administration into the body. While injection (intradermal, intramuscular, intravenous) is an acceptable solution in many cases, having a vaccine product that is orally available will greatly extend its ease of use and applicability on a global scale. For orally administered vaccines, epithelial cells constitute the principal barrier that separates an organism's interior from the outside world. Epithelial cells such as those that line the gastrointestinal tract form continuous monolayers that simultaneously confront the extracellular fluid compartment and the extracorporeal space. Uptake by these gut epithelial cells can be enhanced, and the nanoparticles carried by "transcytosis" to the lymphatics where they have access to dendritic cells.

Through the process of "antigen sampling," underlying mucosal-associated lymphoid tissue sample the environment for the presence of pathogens. This sampling is carried out by an apical to basolateral transcytotic event and is mediated by M cells located in lymphoid follicle-associated epithelium (FAE) throughout the GI tract. In addition, absorptive enterocytes may transport microorganisms or other nanoparticulates to intraepithelial lymphocytes. DCs may perform this function directly, with a population of DCs being intercalated between epithelial cells and extending processes into the gut lumen to sample the microorganisms present.

Adherence to cells is an essential first step in crossing the epithelial barrier by any of these mechanisms. Therefore, in some embodiments, modular nanoparticle vaccines further include epithelial cell recognition elements. Epithelial cell targeting molecules include monoclonal or polyclonal antibodies or bioactive fragments thereof that recognize and bind to epitopes displayed on the surface of epithelial cells. Epithelial cell targeting molecules also include ligands which bind to a cell surface receptor on epithelial cells. Ligands include, but are not limited to, molecules such as polypeptides, nucleotides and polysaccharides.

A variety of receptors on epithelial cells may be targeted by epithelial cell targeting molecules. Examples of suitable receptors to be targeted include, but are not limited to, IgE Fc receptors, EpCAM, selected carbohydrate specificities, dipeptidyl peptidase, and E-cadherin.

Coatings to Inhibit Degradation of Nanoparticle Vaccine Compositions in Extreme pH Environments Vaccine particles administered orally will encounter a corrosive environment in the gastrointestinal (GI) tract with areas of low and high pH, as well as resident degradative enzymes and solubilizing agents. Biodegradable particulates have gained attention as oral vaccines because of their ability to protect antigens on route to immune sites across the intestinal epithelium (O'Hagan and Valiante, 2003, *Nat. Rev. Drug Discov.,* 2:727-35; van der Lubben et al., 2001, *Adv. Drug Deliv. Rev.,* 52:139-44; Wikingsson and Sjoholm, 2002, *Vaccine,* 20:3355-63; Moser et al., 2003, *Expert Rev. Vaccines,* 2:189-96; all of which are incorporated herein by reference). However, while the antigen is protected from environmental elements in transit, little protection is offered to elements coupled to the surface of the particle during the transit to immune effector sites. This protection may be necessary to insure proper particle function and targeting.

For this reason, "shielding" is a desired feature to protect nanoparticle compositions and their immune recognition elements in transit to the GI epithelium. Shielding may be environmentally-sensitive, i.e. pH responsive, or simply a protective layer. In some embodiments, modular nanoparticle vaccines further include pH-sensitive molecules which protect the composition from hydrolysis and degradation in low pH environments. Such pH-sensitive protecting molecules are preferred because subsequent to the particles transit through a low pH environment, upon reaching its destination in the higher pH intestinal site, particles should expose epithelial targeting molecules to allow for specific interactions with target epithelial cells, followed by transcytosis through the epithelium and subsequent interactions with subepithelial dendritic cells.

Exemplary non-pH-sensitive molecules which protect the composition from hydrolysis and degradation in low pH environments are poly(ethylene) glycol, gelatin and albumins.

Exemplary pH-sensitive molecules which protect the composition from hydrolysis and degradation in low pH environments are elastin and poly(methacrylic) acid (PMAA). Both of these molecules are in extended conformations at pH 7.4 and shrink rapidly (within seconds) upon exposure to lower pH environments (below pH 5 for elastin and below pH 5-6 for poly(methacylic) acid). Other pH-sensitive molecules which may be used include poly(acrylic acid), poly(methyl methacrylic acid) and poly(N-alkyl acrylamides), or other enteric coatings discussed above.

In some embodiments, pH-sensitive or pH-insensitive protective molecules are directly coupled to nanoparticles, or may be coupled to nanoparticles through adaptor elements, such as those described above. In some embodiments, the epithelial cell targeting molecules are functionally coupled to adaptor elements.

Adjuvants

In some embodiments, modular nanoparticulate vaccines can include adjuvants. These can be incorporated into, administered with, or administered separately from, the vaccine nanoparticles. Adjuvants may be provided encapsulated or otherwise entrapped in the polymeric core of the nanoparticle vaccine, or may be associated with the surface of the nanoparticle either through direct association with the polymeric core, or through association with adaptor elements. Adjuvant may be in the form of separate nanoparticles or in a suspension or solution administered with the vaccine nanoparticles.

In some embodiments, an adjuvant is synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8+ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

In some embodiments, an adjuvant can be, but is not limited to, one or more of the following: oil emulsions (e.g., Freund's adjuvant); saponin formulations; virosomes and viral-like particles; bacterial and microbial derivatives including, but not limited to carbohydrates such as lipopolysaccharide (LPS); immunostimulatory oligonucleotides; ADP-ribosylating toxins and detoxified derivatives; alum; BCG; mineral-containing compositions (e.g., mineral salts, such as aluminum salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-γ), macrophage colony stimulating factor, and tumor necrosis factor; and co-stimulatory molecules, such as those of the B7 family. Such proteinaceous adjuvants may be provided as the full-length polypeptide or an active fragment thereof, or in the form of DNA, such as plasmid DNA.

Contrast Agents and Other Markers

In some embodiments, modular nanoparticulate vaccine may further include agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DID, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3.

Additionally radionuclides can be used as imaging agents. Suitable radionuclides include, but are not limited to radioactive species of Fe(III), Fe(II), Cu(II), Mg(II), Ca(II), and Zn(II) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

Example 4

Pan-Allergy Vaccine Comprising Nanoparticles Described in the Emory Applications The present Example describes preparation of nanoparticle compositions substantially based on the Emory Applications but incorporating the inventive insight described herein that useful allergy vaccine compositions, and particularly useful multiple-allergy or pan-allergy vaccine compositions, can be prepared without including allergy-specific antigens. The present invention provides the insight that such antigens are not required for beneficial effect and, in fact, that removal of antigens can provide compositions with multiple-allergy or pan-allergy therapeutic and/or prophylactic utility.

As described in the Emory Applications, nanoparticle compositions can desirably be prepared from polyketal polymers, as described in further detail in the sections below, except that nanoparticle compositions in accordance with the present invention do not contain any allergy-specific antigens.

Polyketal Polymers

In some embodiments, provided nanoparticle compositions comprise biodegradable hydrophobic polyketal polymers comprising multiple ketal groups, each ketal group having two oxygen atoms within the polymer backbone. In some embodiments, provided nanoparticle compositions comprise biodegradable hydrophobic polyketal polymers that are in the form of a solid molecule.

In some embodiments, ketal groups include, but are not limited to, 2,2-dioxypropyl group, 2,2-dioxybutyl group, 1,1-dioxycyclohexyl group or dioxyacetophenyl group. In some embodiments, ketal polymers include, but are not limited to, aliphatic, cycloaliphatic and/or aromatic ketals containing one or more hetero-atom, such as nitrogen, sulfur, oxygen and/or halides.

In some embodiments, provided nanoparticle compositions further comprise a compound comprising alkyl, aryl, and/or cycloalkyl groups. In some embodiments, the compound may be directly attached to the ketal group.

In some embodiments, suitable alkyl groups include, but are not limited to, methyl, ethyl and/or butyl groups. In some embodiments, suitable aryl groups include, but are not limited to, substituted and/or unsubstituted benzyl, phenyl and/or naphtyl groups, such as, for example, a 1,4-dimethylbenzene. In some embodiments, suitable cycloalkyl groups include, but are not limited to, substituted or unsubstituted cyclohexyl, cyclopropyl, cyclopentyl groups, such as, for example, 1,4-dimethylcyclohexyl group.

In some embodiments, polyketal polymers are poly(1,4-phenylene-acetone dimethylene ketal). In some embodiments, this polymer can be synthesized of 2,2-dimethoxypropane and 1,4-benzene dimethanol. In some embodiments, polyketal polymers are poly(1,4-cyclohexane-acetone dimethylene ketal), which can be synthesized of 2,2-dimethoxypropane and 1,4-cyclohexane dimethanol.

In some embodiments, polyketal polymers are poly(cyclohexane-1,4-diyl acetone dimethylene ketal) (PCADK). PCADK is made from cyclohexane dimethanol and degrades in an acid sensitive manner into cyclohexane dimethanol and acetone. Ketal linkages in PCADK typically hydrolyze on the order of weeks under physiologic pH conditions. At the phagosomal pH of 4.5, ketal linkages of PCADK are typically approximately 30% hydrolyzed after 10 days.

In some embodiments, polyketal polymers include, but are not limited to, any one or more of PK1, PK2, PK3, PK4, PK5 and PK6 copolymers. In some embodiments, these six polyketal copolymers exhibit varied hydrolysis kinetics at different pH levels. For example at pH 4.5, PK4 is generally the fastest out of the six copolymers to hydrolyze with PK3 generally having the second faster hydrolysis rate. In turn, PK3 generally has faster hydrolysis kinetics than PK2 or PK5, while PK2 and PK5 generally have faster hydrolysis kinetics than PK1 or PK6. However, at pH 7.4, PK3 is generally hydrolyzed faster than PK4. Thus, in some embodiments, by altering the copolymer percentage of polyketals, hydrolysis kinetics for controllable release of an active agent can be fine tuned.

In some embodiments, PK1 has a structure as shown in Table 2 and is made up of at least 2 different monomers i.e., repeating units such as random repeating units. In some embodiments, one type of monomer is 1,4,-cyclohexanedimethoxy with an x value (i.e. percent component of the first monomer incorporated into the polymer) of about 98%, and the second type of monomer is 1,5-pentanedioxy with a y value (i.e. percent component of the second monomer incorporated into the polymer) of about 2%. The n value may be 3. In some embodiments, PK1 is synthesized from two types of starting compounds, namely, 1,4-cyclohexanedimethanol and 1,5-pentanediol. An IUPAC designation for PK1 is poly(cyclohexane-1,4-diyl acetone dimethylene ketal-co-1,5-pentane-acetone dimethylene ketal).

TABLE 2

Exemplary Compositions and Molecular Weights of Polyketal Copolymers

[chemical structure]

n = 2, 3, 4, and 6

| Polymer ID | Polymer Composition | | $M_n$ | DPI |
|---|---|---|---|---|
| | Monomer A | Monomer B | | |
| PK1 | 1,4-cyclohexanedimethanol (x = 98.03%) | 1,5-pentanediol (y = 1.93%) | 2149 | 1.742 |
| PK2 | 1,4-cyclohexanedimethanol (x = 92.46%) | 1,5-pentanediol (y = 7.56%) | 2530 | 1.629 |
| PK3 | 1,4-cyclohexanedimethanol (x = 86.70%) | 1,5-pentanediol (y = 13.30%) | 2596 | 1.432 |
| PK4 | 1,4-cyclohexanedimethanol (x = 96.75%) | 1,4-butanediol (y = 3.25%) | 2637 | 1.553 |
| PK5 | 1,4-cyclohexanedimethanol (x = 85.32%) | 1,6- = hexanediol (y = 14.68%) | 2122 | 1.538 |
| PK6 | 1,4-cyclohexanedimethanol (x = 87.31%) | 1,8-octanediol (y = 12.69%) | 2181 | 1.786 |

In some embodiments, PK2 has a structure as shown in Table 2 and is made up of at least 2 different monomers i.e., repeating units such as random repeating units. In some embodiments, one type of monomer is 1,4,-cyclohexanedimethoxy with an x value (i.e. percent component of the first monomer incorporated into the polymer) of about 92%, and the second type of monomer is 1,5-pentanedioxy with a y value (i.e. percent component of the second monomer incorporated into the polymer) of about 8%. The n value may be 3. In some embodiments, PK2 is synthesized from two types of starting compounds, namely, 1,4-cyclohexanedimethanol and 1,5-pentanediol. An IUPAC designation for PK2 is poly(cyclohexane-1,4-diyl acetone dimethylene ketal-co-1,5-pentane-acetone dimethylene ketal.

In some embodiments, PK3 has a structure as shown in Table 2 and is made up of at least 2 different monomers i.e., repeating units such as random repeating units. In some embodiments, one type of monomer is 1,4,-cyclohexanedimethoxy with an x value (i.e. percent component of the first monomer incorporated into the polymer) of about 87%, and the second type of monomer is 1,5-pentanedioxy with a y value (i.e. percent component of the second monomer incorporated into the polymer) of about 13%. The n value may be 3. In some embodiments, PK3 is synthesized from two types of starting compounds, namely, 1,4-cyclohexanedimethanol and 1,5-pentanediol. An IUPAC designation for PK3 is poly(cyclohexane-1,4-diyl acetone dimethylene ketal-co-1,5-pentane-acetone dimethylene ketal.

In some embodiments, PK4 has a structure as shown in Table 2 and is made up of at least 2 different monomers i.e., repeating units such as random repeating units. In some embodiments, one type of monomer is 1,4,-cyclohexanedimethoxy with an x value (i.e. percent component of the first monomer incorporated into the polymer) of about 97%, and the second type of monomer is 1,4-butanedioxy with a y value (i.e. percent component of the second monomer incorporated into the polymer) of about 3%. The n value may be 2. In some embodiments, PK4 is synthesized from two types of starting compounds, namely, 1,4-cyclohexanedimethanol and 1,4-butanediol. An IUPAC designation for PK4 is poly(cyclohexane-1,4-diyl acetone dimethylene ketal-co-1,4-butane-acetone dimethylene ketal).

In some embodiments, PK5 has a structure as shown in Table 2 and is made up of at least 2 different monomers i.e., repeating units such as random repeating units. In some embodiments, one type of monomer is 1,4,-cyclohexanedimethoxy with an x value (i.e. percent component of the first monomer incorporated into the polymer) of about 85%, and the second type of monomer is 1,6-hexanedioxy with a y value (i.e. percent component of the second monomer incorporated into the polymer) of about 15%. The n value may be 4. In some embodiments, PK5 is synthesized from two types of starting compounds, namely, 1,4-cyclohexanedimethanol and 1,6-hexanediol. An IUPAC designation for PK5 is poly(cyclohexane-1,4-diyl acetone dimethylene ketal-co-1,6-hexane-acetone dimethylene ketal).

In some embodiments, PK6 has a structure as shown in Table 2 and is made up of at least 2 different monomers i.e., repeating units such as random repeating units. In one example of PK6, one type of monomer is 1,4,-cyclohexanedimethoxy with an x value (i.e. percent component of the first monomer incorporated into the polymer) of about 87%, and the second type of monomer is 1,8-octanedioxy with a y value (i.e. percent component of the second monomer incorporated into the polymer) of about 13%. The n value may be 6. In some embodiments, PK6 is synthesized from two types of starting compounds, namely, 1,4-cyclohexanedimethanol and 1,8-octanediol. An IUPAC designation for PK6 is poly(cyclohexane-1,4-diyl acetone dimethylene ketal-co-1,8-octane-acetone dimethylene ketal).

In some embodiments, one or more PK1-PK6 copolymers may be synthesized using the acetal exchange reaction by copolymerizing 1,4-cyclohexanedimethanol with either butanediol, pentanediol, hexanediol or octanediol. As shown in Table 2, a PK1 was synthesized with monomer A (1,4-cyclohexanedimethanol) plus monomer B (1,5-pentanediol); a PK2 was synthesized with monomer A (1,4-cyclohexanedimethanol) plus monomer B (1,5-pentanediol); a PK3 was synthesized with monomer A (1,4-cyclohexanedimethanol) plus monomer B (1,5-pentanediol); a PK4 was synthesized with monomer A (1,4-cyclohexanedimethanol) plus monomer B (1,4-butanediol); a PK5 was synthesized with monomer A (1,4-cyclohexanedimethanol) plus monomer B (1,6-hexanediol); a PK6 was synthesized with monomer A (1,4-cyclohexanedimethanol) plus monomer B (1,8-octanediol).

In some embodiments, PK1, PK2, PK3, PK4, PK5 and/or PK6 copolymers can be intermingled to change or fine tune the release rate profile for attached active agents. For example, a polyketal with fast hydrolysis kinetics (e.g., PK4 or PK3) can be mixed with a polyketal with slower hydrolysis kinetics (e.g., PK1 or PK6) and co-administered to a subject. In general, an active agent joined to PK4 or PK3 will be released in a subject quickly to provide the subject with an immediate release (IR) dose of active agent, while an active agent joined to PK1 or PK6 will be released at a slower rate allowing a gradual or extended release (ER) of the active agent in the subject.

In some embodiments, biodegradable hydrophobic polyketal polymers comprise (1) multiple ketal groups, each ketal group having two oxygen atoms within the polymer backbone and (1) a linker. Ketal groups may comprise a 2,2-dioxypropyl group.

Biodegradable Polyketal Particles

In some embodiments, biodegradable particles comprise one or more polyketal polymers. In some embodiments, particle size can vary. For example, biodegradable particles can be made at nanometer (nm) or micron (µm) scale, e.g., to form nanoparticles or microparticles. In some embodiments, particles range in size from about 50 nm to 1000 µm. In some embodiments, particles range in size from about 200 nm to 600 µm. In some embodiments, particles range in size from about 1 µm to 10 µm, 10 µm to 20 µm, 20 µm to 30 µm, 30 µm to 40 µm or 40 µm to 50 µm. In some embodiments, particles range in size from about 1 µm to 50 µm. In some embodiments, particles are between about 50 and 1000 nm and/or between about 200 and 600 nm. In some embodiments, particle size is about 30 µm.

In some embodiments, suitable polyketal polymers for forming biodegradable particles are between about 0.5 kDa and about 2 MDa, between 1 and about 150 kDa, and/or between about 4 and about 6 kDa. In some embodiments, the number of the monomers in the polymer can range from about 2 to about 20,000, from about 10 to about 1,000, and/or from about 10 to about 50.

In some embodiments, polyketal polymers hydrolyze in aqueous solutions into low molecular weight, water soluble alcohols and ketones. For example, degradation of poly(alkyl-acetone dimethylene ketal) is typically acid-sensitive, e.g., with a half-life of 102.0 h at pH 7.4 and 35.0 h at pH 5.0. In some embodiments, a ketal linkage in a polymeric backbone degrades under acidic conditions of phagosomes, e.g., within 1-2 days at pH 5.0. In some embodiments, polyketals can therefore also be used for targeting the acidic environments of tumors, inflammation and phago-lysosomes. Degradation does not usually generate acidic degradation products. Thus, in some embodiments, ketal polymers are suitable for biological use.

In some embodiments, polyketal polymer particles can further comprise one or more active agents.

In some embodiments, a biodegradable particle comprises: (a) a biodegradable hydrophobic polyketal polymer comprising multiple ketal groups, each ketal group having two oxygen atoms within the polymer backbone and (b) a linker. In some embodiments, suitable polymers include, but are not limited to, PCADK and PK1-PK6.

In some embodiments, a polyketal polymer particle can further comprise one or more linkers which can bind an active agent. Multiple linkers of the same or different types can be attached to a polymer particle. In some embodiments, linkers are attached to particle surfaces. In some embodiments, linkers are exposed to solvent or aqueous solution surrounding the particles.

In some embodiments, a biodegradable particle comprises (a) one or more of PK1, PK2, PK3, PK4, PK5 and/or PK6 (which can optionally comprise a linker), and (b) an active agent. In some embodiments, a biodegradable particle comprises (a) PCADK (which can optionally comprise a linker) and (b) an active agent.

In some embodiments, particles can comprise a single population of polyketals and/or a mixed population.

Micelles

The present invention provides biodegradable crosslinked micelles comprising multiple polymers. In some embodiments, polymers are crosslinked by an external crosslinking agent. External crosslinking agents as used herein are agents which are not introduced into the polymer chain. In some embodiments, use of external agents results in a faster crosslinking reaction compared to a reaction wherein only crosslinkable moieties within the polymer are used. In some embodiments, an external crosslinking agent reduces the probability that an encapsulated protein will be destroyed.

In some embodiments, suitable crosslinking agents include, but are not limited to, compounds which comprise at least two thiol groups. In some embodiments, suitable crosslinking agents include, but are not limited to, ethylene glycol dithiol, aliphatic dithiols, dithiols which are connected by ketal linkages, and diamine containing molecules. In general, thiol groups are sensitive to reducing conditions, thus enabling an easy degradation of the micelle. In some embodiments, crosslinking strategies include, but are not limited to, crosslinking by amines, esters, carbonates, thio-esters, Schiff bases, vicinal diols, alkenes and alkynes, ketals, ketals orthoesters, thio-ketals, thio-orthoesters, silyketals, phenyl boronic acid-diol complexes, carbon-carbon bonds, sulfones, phosphate containing functional groups, azides, enzyme cleavable linkages, and/or urethanes (O'Reilly et al., 2005, *Chem. Mater.*, 17:5976-88; Hanker et al., 2005, *Science*, 309:1200-05; Le et al., 2005 *Langmuir*, 21:11999-12006, Example 1, FIG. 9; all of which are incorporated herein by reference).

In some embodiments, an external crosslinking agent comprises an antigen. In some embodiments, suitable antigens include, but are not limited to, proteins or peptides. In some embodiments, antigens are naturally occurring, chemically synthesized or recombinantly made. In some embodiments, suitable protein or peptide antigens include, but are not limited to, HIV antigens such as gp120 protein (or fragment thereof), TAT protein (or fragment thereof), NEF protein (or fragment thereof), HCV protein (or fragment thereof), and env protein (or fragment thereof). In some embodiments, an antigen includes a gp120 peptide antigen chemically synthesized and modified to contain four additional cysteine residues to create therein additional disulfide bonds. In some embodiments, antigen having crosslinkable groups can be used. In some embodiments, antigens not having or having few crosslinkable groups can be modified (e.g., chemically modified) to comprise crosslinkable thiol groups, azides, alkynes, amines, maleimides, vinyl sulfones, ketones, hydrazines and/or thioesters.

In some embodiments, polymers for micelle formation can be homopolymers or copolymers, such as block copolymers or graft polymers. In some embodiments, suitable polymers include, but are not limited to, PEG block copolymers, such as PEG-polyamino acids, for example, PEG-polylysine, PEG-polyglutamic acid, PEG-polyaspartic acid or PEG-polyarginine; PEG-polyesters, PEG-polyurethane, PEG-PPO, modified or unmodified, PEG-polyacrylate or PEG-polymethacrylate, synthesized by atom transfer polymerization, where the PEG acts as an initiator. To facilitate polymer crosslinking, a polymer can be modified to include chemical groups including, but not limited to, amines, esters, carbonates, thioesters, Schiff bases, vicinal diols, alkenes and alkynes, ketals, ketals orthoesters, thioketals, thio-orthoesters, sily-ketals, phenyl boronic acid-diol complexes, carbon-carbon bonds, sulfones, phosphate containing functional groups, azides, enzyme cleavable linkages, and/or urethanes. In some embodiments, these groups can be introduced via chemical reactions known in the art, such as, among others, Michael addition or acylation (Example 1, FIG. 9). In some embodiments, a modified polymer is PEG-polylysine thiopyridal (FIG. 9).

In some embodiments, a polymethacrylate or polyacrylate block can contain modifications to allow for assembly with vaccine components and crosslinking. In some embodiments, a polyacrylate block can be a block copolymer consisting of polydimethylamino-acryalte-poly-glycidyl acrylate. In some embodiments, a homopolymer of random copolymers composed of various acrylate or methacrylate monomers capable of forming micelles with vaccine components can be used.

In some embodiments, micelles can further comprise one or more active agents. In some embodiments, suitable active agents are described in the previous section.

In some embodiments, an interaction between a micelle and an active agent can be electrostatic or hydrophobic or can occur due to hydrogen bond formation or molecular recognition depending on the type of polymer and agent. In some embodiments, the surface of a micelle is modified to contain targeting groups such as, for example, antibodies against dendritic cells, proteins which stimulate subsets of dendritic cells, and/or macrophages such as CD40L, DEC-205, CD11c, langerin, MARCO, 33D 1, etc.

In some embodiments, micelles are designed to deliver peptide antigens and immunomodulatory molecules to antigen-presenting cells (APCs). In some embodiments, micelles comprise immunomodulatory molecules, peptide antigens and a copolymer. In some embodiments, a peptide antigen acts as a crosslinker which allows the peptide antigen to be efficiently encapsulated into the peptide crosslinked micelles (PCMs) and also stabilizes them against degradation by serum components In some embodiments, a micelle can be used to encapsulate peptide or protein antigens together with immunomodulatory agents including multiple TLR ligands, or molecules such as synthetic compounds or siRNA that modulate signaling networks within cells (e.g., dendritic cells or other antigen presenting cells). In some embodiments, a micelle targets dendritic cells and macrophages through their nanometer dimensions, as such cells robustly internalize nanometer sized materials, through phagocytosis. In some embodiments, micelles are crosslinked by crosslinking agents comprising disulfide linkages, which can stabilize them against decomposition induced by serum proteins. In some embodiments, a micelle has a size of 5 to 50 microns.

In some embodiments, polymers forming micelles further comprise a linker. In some embodiments, a linker allows for dual delivery of one or more active agents, via encapsulation of the active agents by a micelle or attachment to a micelle.

In some embodiments, after phagocytosis, biodegradable particles and micelles break down, and encapsulated material such as peptide or antigens, and immune stimulatory agents [e.g.: ISS DNA, TLR 7/8, TLR 3 ligands such as ss RNA, TLR 2 ligands, and inhibitors of regulatory pathways such as the ERK, c-Fos or Foxp3 pathway], are released into a dendritic cell, or macrophage, and the immunomodulatory agent will induce the antigen-presenting cells, to secrete a variety of cytokines. This combination of signals will frequently result in optimal activation of T cells, and/or inhibition of regulatory T cells and dendritic cells.

In some embodiments, micelles can include active agents such as vaccines composed of antigens from the relevant pathogen, together with immune modulatory agents [e.g.: ISS DNA, TLR 7/8 ligands such as ss RNA, TLR 2 ligands, and inhibitors of regulatory pathways such as inhibitors of ERK, c-Fos or Foxp3, PI3 kinase, Akt, SOCS 1-7 proteins, or siRNA molecules or antisense molecules that inhibit such regulatory pathways].

The invention provides methods for reversibly modifying proteins so that they have an appropriate charge to be encapsulated in the micelles. In general, this strategy is based on reacting amine groups of a protein with a compound, generating additional negative charges for every amine group, and rendering the protein negative. A modified protein is then encapsulated in a micelle, crosslinked, and then pH is reduced in order to remove the inserted compound form the protein. In some embodiments, a compound with amine groups is cis-aconityl. This group typically adds negative charges to each amine group and can be released at pH 4.0.

In some embodiments, for targeting strategies include synthesizing a heterobifunctional PEG that has a DNA binding domain at one end and another end that can attached to a protein. This PEG chain is then attached to a protein and assembled into preformed micelles that contain immunostimulatory DNA. In some embodiments, DNA binding domains include acridine and/or polyacridines. In some embodiments, targeting ligands include galactose, mannose phosphate, mannose, peptides, and/or antibodies.

Further Modifications of Biodegradable Particles and Micelles

In some embodiments, biodegradable particle and/or micelles are modified to incorporate antibodies or other molecules which target (1) specific receptors on particular subsets of DCs or macrophages or monocytes, including Langerhans cells, dermal DCs, myeloid DCs, plasmacytoid DCs, etc. and/or (2) specific receptors on antigen-presenting cells, such as DEC205, Langerin, DC-SIGN, dectin-1, 33D1, MARCO, etc.

Methods of Producing Particles and Micelles

In some embodiments, methods of producing particles and/or micelles comprise steps of a) forming a hydrophobic polymer of a ketal and a diol or an unsaturated alcohol; b) forming a polymer particle of the polymer of a) in the presence of one or more active agents and thereby encapsulating the agent(s). Examples of suitable chemistries for forming the hydrophobic polymer of a ketal and a diol or an unsaturated alcohol include acetal exchange reaction using single or double emulsions and acyclic diene metathesis (Heffeman and Murthy, 2005, *Bioconjug. Chem.*, 16:1340-2; Jain, 2000, *Biomaterials*, 21:2475-90; Wagener and Gomez, "ADMET Polymerization," in *Encyclopedia of Materials: Science and Technology*, E. J. Kramer and C. Hawker, Editors, Elsevier, Oxford, 5, 48 (2002); all of which are incorporated herein by reference).

In some embodiments, suitable ketals include, but are not limited to, 2,2-dimethoxypropane, 2,2-dimethoxybutane, 1,1-dimethoxycyclohexane or dimethoxyacetophenole. In some embodiments, suitable ketal polymers include aliphatic, cycloaliphatic and/or aromatic ketals containing one or more hetero-atom, such as nitrogen, sulfur, oxygen and/or halides.

In accordance with the practice of the invention, a diol can be any of alkyl, aryl and/or cycloalkyl diols.

In some embodiments, suitable diols include, but are not limited to, 1,4-benzenedimethanol, 1,4-cyclohexanedimethanol, 1,5-pentane diol, 1,4-butane diol and/or 1,8-octane diol.

In some embodiments, methods for producing particles comprise steps of (a) forming PCADK polymer; and (b) forming a particle of PCADK in the presence of one or more active agents, thereby producing particles. A PCADK polymer can optionally comprise a linker.

In some embodiments, methods for producing the particles comprise steps of (a) forming PK1, PK2, PK3, PK4, PK5 and/or PK6 polymer; and (b) forming a particle of one or more of PK1, PK2, PK3, PK4, PK5 and/or PK6 in the presence of one or more active agents, thereby producing particles. PK1-PK6 polymers can optionally comprise a linker.

In some embodiments, micelles are produced in a two step process. In general, first, polymers are contacted with a liquid (polar or nonpolar liquid depending on the polymer to be used) under appropriate conditions so as to form a micelle. After micelle formation, micelles can be crosslinked with an external crosslinking agent to produce biodegradable micelles.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method of treating allergy, the method comprising:
administering a pharmaceutical composition to a subject suffering from or susceptible to allergic reaction to a particular allergen, such that at least one of the subject's symptoms of allergy are reduced or delayed, wherein:
(i) the pharmaceutical composition comprises a population of nanoparticles formed from at least one polymer, which nanoparticles comprise at least one microbial mimic entity,
wherein the at least one microbial mimic entity is a pathogen-associated molecular pattern (PAMP);
(ii) the pharmaceutical composition is substantially free of the particular allergen; and
(iii) the pharmaceutical composition is formulated for delivery to the subject, and
wherein the administering does not also comprise administering the particular allergen.

2. The method of claim 1, wherein the step of administering is performed via a mode of administration selected from the group consisting of oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical, transdermal, mucosal, intranasal, buccal, enteral, vitreal, sublingual administration, by intratracheal instillation, by bronchial instillation, and by inhalation.

3. The method of claim 1, wherein the step of administering comprises administering multiple individual doses to the subject over a specified period of time.

4. The method of claim 1, wherein the at least one polymer is PLGA.

5. The method of claim 1, wherein the PAMP comprises at least one entity associated with an outer surface of a bacterial cell.

6. The method of claim 5, wherein the at least one entity associated with the outer surface of a bacterial cell is selected from the group consisting of: bacterial lipopolysaccharide, bacterial flagellin, lipoteichoic acid from gram positive bacteria, diacyllipopeptides, triacyllipopeptides, lipopeptide Pam3CysSK4, zymosan from yeast cell wall, peptidoglycans, double-stranded RNAs, unmethylated CpG motifs, heat shock proteins, taxol, viral double-stranded RNA, viral single-stranded RNA, double-stranded DNA, haemozoin, characteristic portions thereof, and/or combinations thereof.

---

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5
```

7. The method of claim 5, wherein the at least one entity associated with the outer surface of a bacterial cell is selected from the group consisting of: bacterial lipopolysaccharide, bacterial flagellin, lipoteichoic acid from gram positive bacteria, peptidoglycan, double-stranded RNAs, unmethylated CpG motifs, any TLR ligands listed in Table 1, characteristic portions thereof, and/or combinations thereof.

* * * * *